United States Patent [19]

Funk et al.

[11] Patent Number: 4,584,655
[45] Date of Patent: Apr. 22, 1986

[54] MOISTURE TESTER

[75] Inventors: David B. Funk, Auburn; David M. Beams, Virden; Dennis E. Grim, Springfield, all of Ill.

[73] Assignee: Dickey-john Corporation, Auburn, Ill.

[21] Appl. No.: 504,134

[22] Filed: Jun. 14, 1983

[51] Int. Cl.⁴ .................. G01N 25/56; G01R 27/26
[52] U.S. Cl. ............................ 364/550; 73/73; 324/61 R; 364/482
[58] Field of Search ............ 73/73, 74; 324/61 R; 364/482, 550, 556; 377/12, 15, 16, 19

[56] References Cited

U.S. PATENT DOCUMENTS

| | | | |
|---|---|---|---|
| 2,693,575 | 11/1954 | Greenwood et al. | 324/61 R |
| 3,566,260 | 2/1971 | Johnston | 324/61 R |
| 3,691,457 | 9/1972 | Kriellaars | 324/61 R |
| 3,739,264 | 6/1973 | Resh | 324/61 R |
| 3,760,267 | 9/1973 | Williams | 324/61 R |
| 3,778,707 | 12/1973 | Vogel | 324/61 R |
| 3,781,673 | 12/1973 | Resh | 324/61 R |
| 3,794,911 | 2/1974 | Fathauer | 324/61 QS |
| 4,021,733 | 5/1977 | Green et al. | 324/61 R |
| 4,050,016 | 9/1977 | Marsh et al. | 324/61 R |
| 4,058,766 | 11/1977 | Vogel et al. | 324/61 R |
| 4,080,563 | 3/1978 | Marsh et al. | 324/61 R |
| 4,121,151 | 10/1978 | Funk et al. | 324/61 R |
| 4,147,976 | 4/1979 | Wang | 324/61 R |
| 4,168,466 | 9/1979 | Boldt | 324/61 R |
| 4,193,116 | 3/1980 | Funk | 364/556 |
| 4,257,324 | 3/1981 | Stefansson et al. | 377/15 X |
| 4,354,244 | 10/1982 | Miller et al. | 364/556 |

Primary Examiner—Errol A. Krass
Assistant Examiner—Edward R. Cosimano
Attorney, Agent, or Firm—Trexler, Bushnell & Wolters, Ltd.

[57] ABSTRACT

A measurement apparatus is provided for use with a moisture tester of the type wherein the moisture content of a sample is determined as a function of the change in capacitance of a sample-receiving test cell when a sample is present therein from the capacitance of said test cell when empty. The tester also includes a reference oscillator and a test cell oscillator in circuit with the test cell, and a variable capacitor coupled in circuit with the test cell and the oscillators for bringing respective outputs of the two oscillators into a balanced condition both with the test cell empty and with a sample present in the test cell. The variable capacitor comprises a fixed member and a movable member which is rotatable through 360 degrees relative to the fixed member. The measurement apparatus comprises a stepping drive coupled with the rotatable member for incrementally rotating the movable member a predetermined number of steps of equal angular extent per revolution; a control circuit is provided for incrementally energizing the stepping drive in a predetermined fashion to achieve incremental rotation thereof. The control circuit also defines a predetermined and repeatable base position of the movable member with respect to the fixed member. A counting circuit counts the number of steps of the stepping drive during rotation of the movable member between the base position and any other position with respect to said fixed member; whereby the capacitance value between any two given settings of the variable capacitor may be determined as a function of the number of steps counted by the counting circuit during rotation between the base position and each of the given settings, respectively.

26 Claims, 10 Drawing Figures

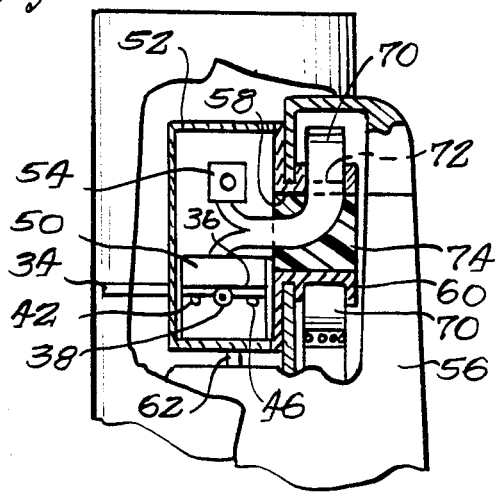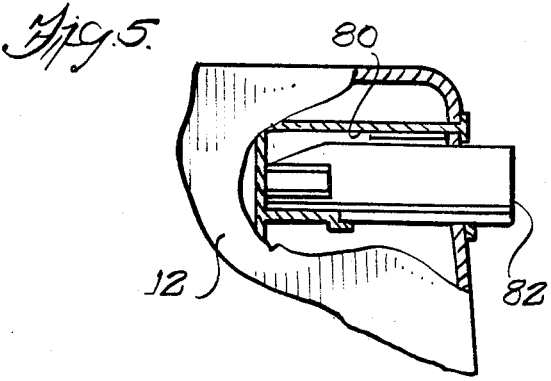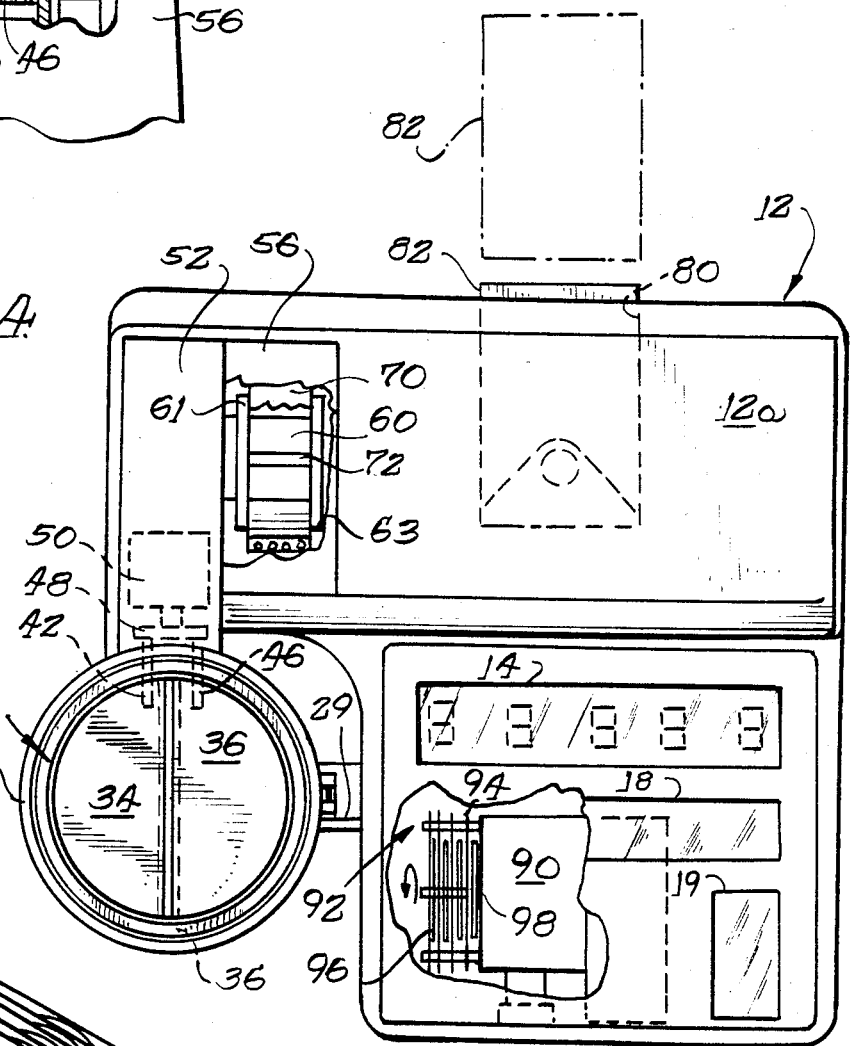

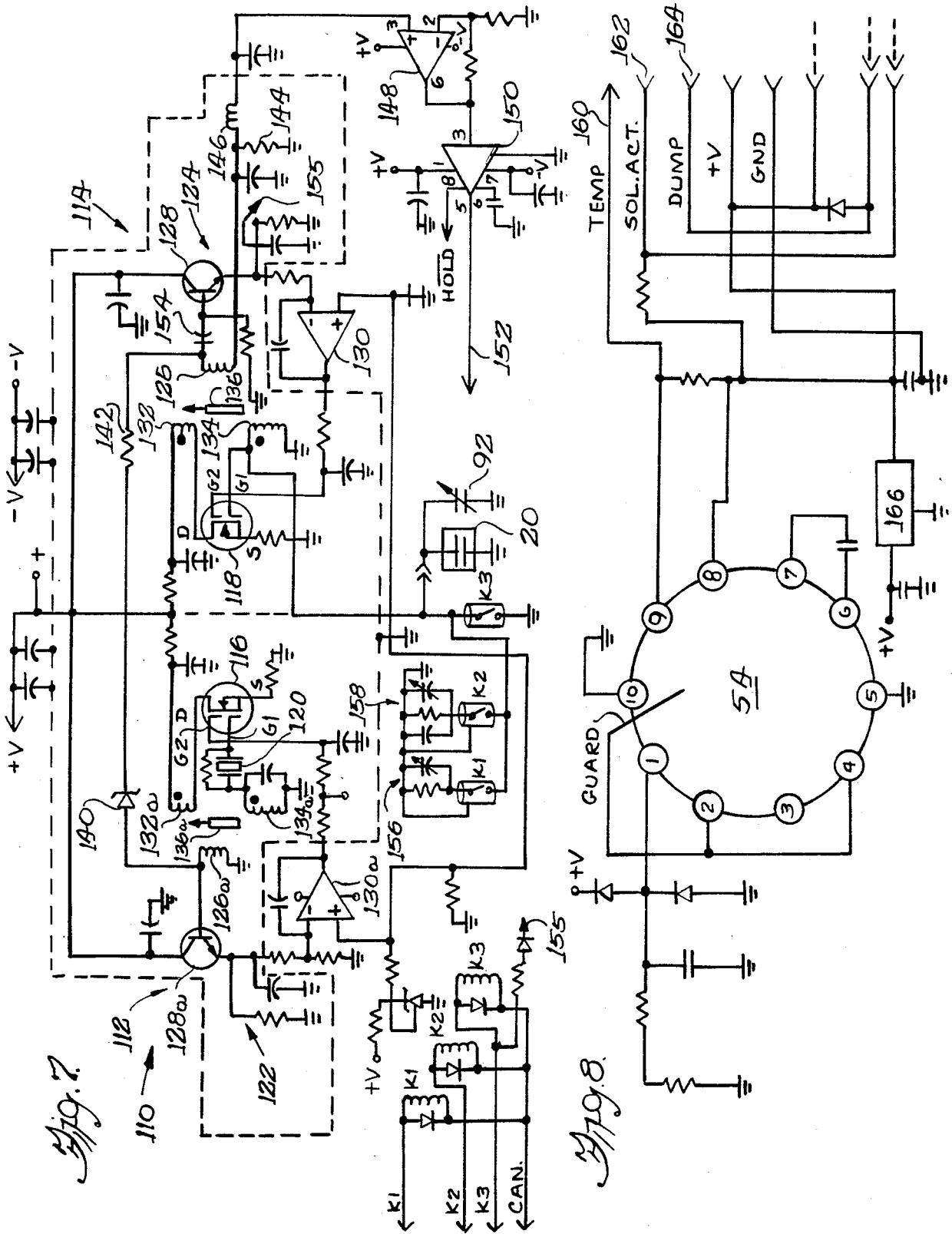

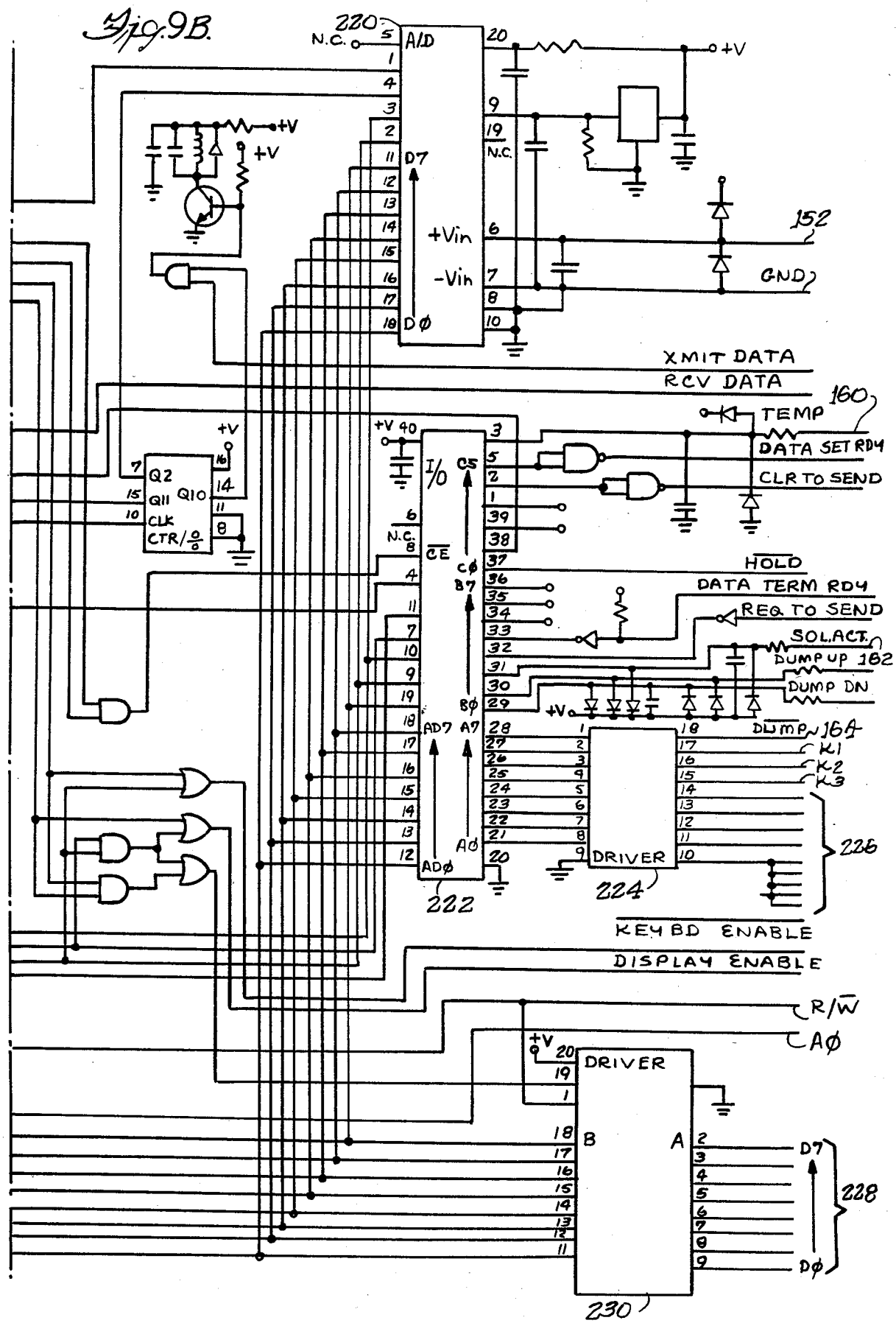

MOISTURE TESTER

BACKGROUND OF THE INVENTION

The present invention is directed generally to the area of test apparatus and more particularly to a moisture tester for determining the moisture content of materials such as grains.

Testing the constituent contents, and especially the moisture content of various agricultural grain products is well known. The prior art has devised a number of novel apparatus for more or less automating the moisture content determination procedure. In this regard, it is desirable in many applications to test the moisture content of a great number of samples of grains in a minimum amount of time.

One particularly successful prior art device is the "model 919" TM moisture meter manufactured by Motomco, Inc. This moisture tester essentially determines the moisture content of a sample of material by determining its dielectric constant or capacitance. In this regard, a premeasured quantity of material is fed to a test cell which essentially comprises a capacitor. Since, the capacitance value of the test cell is determined by the dielectric properties of the sample of material contained therein, the capacitance of the material itself may be inferred from the observed change in capacitance over that of the empty test cell.

More specifically, the foregoing prior art device utilized a substitution method for obtaining the moisture content of the material. That is, the capacitance value of the test cell itself is initially determined, and thereafter a sample of material is introduced into the test cell, whereupon the capacitance thereof is again determined. Hence, the change in capacitance may be attributed to the sample of material, whereby its moisture content may be determined on the basis of known correlations between dielectric properties and moisture content for each particular material. These known correlations have been determined by empirical studies for each of a plurality of different grain materials.

Still more particularly, the prior art method utilized a balanced oscillator approach, whereby the test cell was included in the tank circuit of one oscillator, which was then "balanced" by means of a variable capacitor with a relatively stable reference oscillator. Accordingly, the circuit was once balanced with the empty test cell and again balanced with the sample of material to be tested residing in the test cell. Thereupon, the difference in capacitance value of the variable capacitor at each balance or "null point" could be taken as equal to the capacitance value and hence moisture content of the sample of material.

While the foregoing method and apparatus has found widespread commercial acceptance, there is room for further improvement. For example, with the "moisture meter" referred to above a meter was coupled to the two oscillators so as to give a minimum or "null" reading upon reaching a balanced condition. An indicator and a calibrated dial or scale was associated with the variable capacitor. Thus, a reading of the dial setting necessary to "null" the meter was noted, and a corresponding moisture content taken from a printed chart. A plurality of such charts were provided, one for each of a plurality of different grain products which might be tested. However, in the absence of a suitable chart, or in the case of a moisture content not within the range of adjustment of the variable capacitor, the unit would be incapable of obtaining the desired results.

Moreover, obtaining a reasonably accurate moisture determination, that is, within plus or minus one percent or better, requires a high degree of resolution in the dial or scale associated with the variable capacitor. In this regard, such resolution may be required down to the order of tenths of picofarads. The foregoing problems may be approached by the provision of a larger variable capacitor, however, such capacitors are not inherently linear. Moreover, with a larger capacitor, the exact null point or point of balance between the oscillators becomes increasingly less well defined, and hence proper observation of the meter becomes difficult. Also, the problem of mechanical variance or play in the indicator shaft, etc. intermediate the variable capacitor itself and the dial or scale may be a source of error. Moreover, resolution of the machine to a high degree of accuracy involved the provision of very fine dial divisions, often requiring the use of a magnifying glass to read and thus inviting further error.

Additionally, such accuracy requires a relatively stable and reliable circuit. In the foregoing prior art device a vacuum tube circuit was utilized in conjunction with a highly stable RC reference or calibration network for calibrating the instrument. While it is theoretically possible to replace vacuum tubes with solid-state devices such as FET's the substitution cannot be made without further circuit modifications. For example, while vacuum tube oscillators are reasonable linear with low harmonic distortion, solid-state or FET-based oscillators are generally noticeably more non-linear with significant harmonic distortion. In other respects, the output voltages developed in the pickup links in the vacuum-tube based oscillator circuits are effected by the transconductance of the tubes. This is of course eliminated with the substitution of solid-state devices.

Additionally, as previously noted, under certain conditions, for example, where moisture content and hence capacitance is relatively large, the "null" reading on the meter of the foregoing prior art device is not particularly well defined. Hence, some error may be introduced by inability of the operator to accurately determine by observation of the meter the exact point of balance between the oscillators.

As an additional matter, the mechanical aspects of the prior art device included a first tubular receptacle into which a premeasured quantity of the grain to be tested is introduced. This receptacle was then placed coaxially over the like-dimension tubular test cell and a pair of doors therein manually released to release the premeasured sample to the test cell. In order to minimize the handling of the sample of material and further insure accuracy, it is desirable to automate the foregoing procedure to some extent. In this regard, the prior art meter also required reference to temperature charts and separate measurement of the temperature of a sample to provide a correction factor for the moisture reading. In this regard, the first or "dial-reading" charts were established for a predetermined standard temperature, and hence variations in the actual temperature of the grain required reference to yet a further temperature correction chart. It is also desirable to automate this procedure.

OBJECTS AND SUMMARY OF THE INVENTION

Accordingly, it is a general object of the invention to provide a novel and improved moisture tester which substantially avoids the problems of the prior art devices, while maintaining the advantageous features thereof.

A more specific object is to provide a moisture tester of the foregoing type which provides a higher degree of resolution over a broader range of measurements than heretofore obtainable, while maintaining a surprisingly high degree of accuracy.

A related object is to provide such a moisture tester which provides a direct readout of moisture content of a sample under test without the necessity of referring to charts, conversion tables, or the like.

A related object is to provide an instrument in accordance with the foregoing object which provides such a direct readout, further taking into account both the type of material under test and the temperature thereof.

A further object is to provide an instrument in accordance with the foregoing objects wherein calibration of the instrument for the material under test and determination of the temperature of the sample are automatically accomplished.

A related object is to provide a test instrument in accordance with the foregoing objects which is surprisingly simple and inexpensive in its manufacture and design and yet highly reliable in operation.

BRIEF DESCRIPTION OF THE DRAWINGS

The foregoing, as well as other objects, features and advantages of the invention will be more readily appreciated upon reading the following detailed description of the illustrated embodiment, together with reference to the accompanying drawings, wherein:

FIG. 3 is a partial front elevation, partially in section and partially broken away, illustrating further features of the moisture tester of the invention;

FIG. 4 is a top plan view, partially in section and partially broken away, of the moisture tester of the invention;

FIG. 5 is a partial side elevation, partially in section and partially broken away, showing further details of the moisture tester;

FIG. 6 is a perspective view illustrating further details of a portion of the moisture tester of the previous figures;

FIG. 7 is a schematic circuit diagram of first or oscillator circuit of the invention;

FIG. 8 is a schematic circuit diagram of a second or temperature circuit of the invention; and FIGS. 9A and 9B taken together form a schematic circuit diagram of a further or control circuit of the invention.

DETAILED DESCRIPTION OF THE ILLUSTRATED EMBODIMENT

Figure 1:
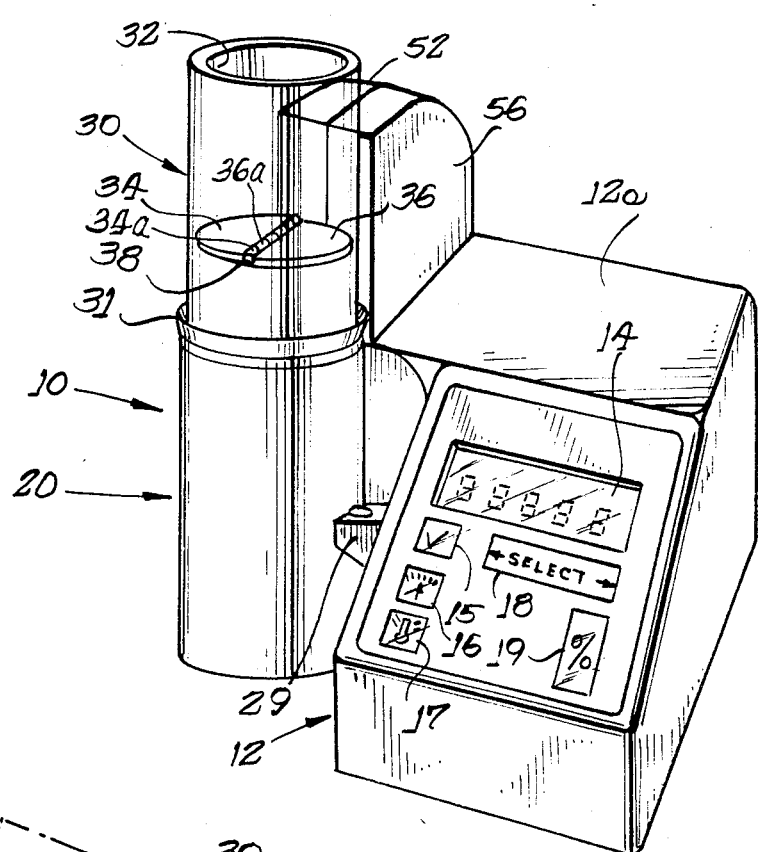
FIG. 1 is a perspective view of a moisture tester in accordance with the invention.

Referring now to the drawings and initially to FIGS. 1-6, various novel features of the mechanical apparatus and the method in accordance with the invention will be described with reference to a moisture tester or "unit" in accordance with the invention, designated generally by the reference numeral 10.

Initially, it will be seen that the moisture tester or unit 10 comprises a base or housing portion designated generally 12 which bears a suitable display 14 and controls 15, 16, 17, 18, and 19 on its face. A generally conventional test cell 20 includes a cylindrical outer wall or electrode 22 and a coaxially mounted inner or center electrode 24. In accordance with conventional practice, this test cell 20 operates essentially as a capacitor, whereby the capacitance or dielectric properties of a material to be tested may be determined by placing the material within the test cell 20. To this end, the test cell 20 further has an open top end 26 and a closed bottom end 28. The test cell 20 is both physically and electrically coupled with the base or housing 12, preferably by removable means, as indicated generally at 29. Accordingly, upon completion of testing of a given sample of material, the test cell 20 may be physically removed from the housing to dispose of the sample of material and ready the test cell for a further sample of material to be tested therein.

To this end, a dump cell designated generally by the reference numeral 30 is provided. Preferably, in accordance with the testing method of the invention, this dump cell 30 is initially filled with a premeasured sample of material. In this regard, it is preferred that a predetermined, accurately weighed sample of material be provided for testing in each instance, to assure uniformity and repeatability of moisture measurements from sample to sample.

Accordingly, a premeasured, predetermined weight of sample material is introduced into an open upper end 32 of the dump cell 30. Preferably dump cell 30 is an open-ended, tubular, cylindrical body of substantially similar diameter to the diameter of the test cell outer wall or electrode 22 and is constructed of a transparent plastic material. This latter outer wall 22 is preferably flared somewhat at its upper end as indicated at reference numeral 31 to receive the lower end of the dump cell 30 to assure transfer of the material therebetween.

Additionally, the dump cell 30 is provided with a pair of pivotally mounted, generally semi-circular door members 34, 36 in its lower interior portion. These doors will be seen to be pivotally or hingedly mounted at their central portions with respect to the tubular cell 30 by a suitable hinge pin, shaft or rod 38. Suitable hinge knuckles or sleeves 34a, 36a are provided in the respective door members 34 and 36 for receiving this hinge pin or rod 38.

Normally the doors 34 and 36 are held in a closed condition by a pair of stops or pins 42, 46 which extend through suitable openings provided therefor in a sidewall of the dump cell 30. These pins 42 and 46 are in turn coupled by a suitable yoke 48 to be controlled by an electrically operated solenoid 50. This solenoid 50 is carried in a suitable housing 52 which is coupled to the side of the dump cell 30. In accordance with a further preferred feature of the invention, a suitable temperature sensor or probe 54 is also mounted in the housing 52 so as to extend into the material received above the doors 34 and 36 in the dump cell 30. In this regard, preferably the temperature of the sample of material weighed and placed in the dump cell 30 is measured therein prior to the opening of the doors 34 and 36 to introduce the material into the test cell 20. As will be seen later, an automated sequence of operations is controlled by the circuits of FIGS. 9A and 9B, which accomplishes temperature measurement and door release in the proper sequence.

In accordance with a further feature of the invention, the housing 52 and hence dump cell 30 coupled thereto are pivotally mounted to a suitable vertically extending support member 56 which is in turn rigidly mounted to an upper surface 12a of the housing 12. This support 56 is provided with a suitable and preferably circular bearing surface 58 for pivotally or rotatably receiving therethrough a shaft member 60 which is coupled to one side of the housing 52. The shaft 60 is preferably generally cylindrical and includes suitable flanges 61, 63. The flange 61 preferably engages or abuts the surface 58 to hold the shaft assembled therewith. Accordingly, the dump cell is preferably manually rotated on shaft 60 about the bearing 58 following release of the doors 34, 36, to allow the doors to again return to their closed position by gravity. This rotation is of course less than 360 degrees and preferably on the order of 120 degrees in angular extent. Suitable sensors 62, 64 which may be, for example, leaf-type miro-switch elements, sense the two extremes of rotation of the dump cell 30 and housing 52. It is noted that the temperature sensor 54 has not been illustrated in FIG. 4 in order to more clearly show the solenoid 50, pins 42, 46 and related structure. Responsive control circuits to be described later, cause the solenoid 50 to withdraw and reinsert the pins 42, 46 so as to control the doors 34 and 36 in conjunction with this manual rotation of dump cell 30. The doors are thus normally held in the closed position for receiving and holding a sample of material in the dump cell 30, until it is time to introduce the sample into the test cell 20. This automated sequence of operation will be further described later with reference to the control circuitry of the invention.

Figure 2:
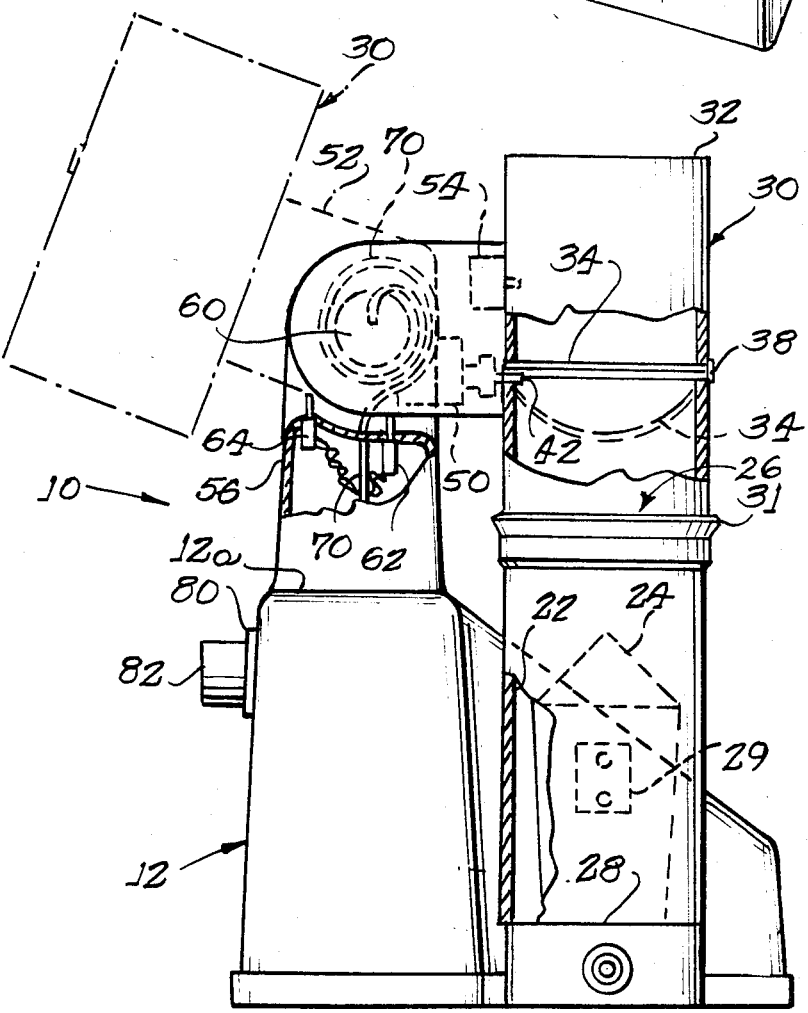
FIG. 2 is an enlarged side elevation, partially in section and partially broken away, of the moisture tester of FIG. 1.

In accordance with a further feature of the invention, electrical signals are fed to and from the solenoid 50 and temperature sensor 54 by a novel, non-stressed or "stress free" cable mounting arrangement. In this regard, a flat or ribbon-type multiple conductor cable 70 is provided from the control circuits mounted within housing 12 and extends into support member 56. This cable 70 is fed through an axially extending slot 72 through the shaft 60 which is a substantially tubular or hollow and preferably cylindrical body. The cable 70 is thereupon fed axially through the interior of the shaft 60 to the solenoid 50 and temperature sensor or probe 54. Preferably, a quantity of suitable packing material 74 is provided about the portion of cable 70 within the shaft 60 to prevent relative frictional engagement therebetween as might otherwise occur upon rotation of the shaft 60. Advantageously, the portion of the cable 70 extending outwardly of the slot 72 is then wrapped substantially one and one-half times circumferentially about the shaft 60 as best seen in FIG. 2. In operation, then, the wrapped portion of the cable 70 acts substantially like a clock spring, tightening somewhat as the dump cell 30 and housing 52 are rotated backwardly as viewed in FIG. 2 about the support member 56 and unraveling somewhat in response to opposite rotation for delivering the dump cell 30 to the rest position at the top of test cell 20. Accordingly, it will be seen that substantially no stress is experienced in the cable 70 itself during this rotation.

As will be more fully described later with reference to the control circuits of the invention, the housing also includes a suitable aperture 80 for receiving one of a plurality of plug-in modules such as a module 82. Briefly, these modules permit the unit 10 to be utilized for obtaining moisture readings in any of a plurality of different materials, without the need for extensive recalibration procedures or any other modification thereto. In this regard the plug-in module 82 contains a suitable solid-state memory component which carries necessary calibration and other data or information for enabling the moisture tester of the invention to measure the moisture content of a given material. It is contemplated that one such plug-in module 82 may be provided for each material to be tested.

Referring now also to FIG. 6 and in accordance with a further feature of the invention, a novel stepping control or drive arrangement for controlling the position of a variable capacitor is designated generally by the reference numeral 90. In this regard, a variable capacitor 92 is generally of the variety having a first plurality of fixed plates 94 and a second plurality of relatively movable plates 96 which are preferably rotatable about 360 degrees for intermeshing engagement with respect to the fixed plates 94. To this end, a suitable drive shaft 98 couples the rotatable or relatively movable plates 96 to a gear train comprising a sprocket-type gear 100 driven by a worm-type gear 102. In the illustrated embodiment, the gear ratio provided is 50 to 1.

In accordance with a feature of the invention, a stepper or stepping motor 104 is provided for rotating the worm gear 102 by way of a suitable shaft 106. Preferably the motor 104 is a model 82201-P2 "stepper motor" available, for example, form AirPax, Cheshire division, Cheshire, CT 06410. As is known in the art, such a stepping motor may be conventionally driven to provide substantially 7½ degree steps, so as to achieve 48 steps per 360 degree revolution thereof. However, the motor 104 is preferably controlled by the circuits of FIGS. 9A and 9B to be described later, so as to achieve "half steps" of substantially 3¾ degrees each, thereby achieving 96 steps about the 360 degrees of revolution thereof. Accordingly, with the 50 to 1 ratio provided by the gears 100, 102, it will be seen that the variable capacitor 92 in accordance with the present invention has 4800 definable steps or positions about 360 degrees of rotation of plates 96 with respect to plates 94. It will be appreciated that the foregoing arrangement provides a heretofore unobtainable degree of resolution in measuring the position, and by extension, the capacitance value at any given position or setting of the capacitor 92.

The operation of the foregoing will be more readily understood with reference to the operation of certain circuits as will next be described with reference to FIG. 7.

In FIG. 7, an oscillator or test cell circuit in accordance with the invention is designated generally by the reference numeral 110. This circuit 110 includes a reference oscillator circuit designated generally 112 and a test cell oscillator circuit designated generally 114.

In accordance with the prior art method, the reference oscillator 112 and test cell oscillator 114 are inductively coupled in a common inductive loop, whereby some amount of energy is extracted from each oscillator and used to operate a null detection circuit (to be discussed later), which may operate in the fashion of a milliammeter ("meter"). Essentially, the capacitance of test cell 20 is placed in the tank circuit of the test cell oscillator 114, in parallel with the variable capacitor 92. Thereupon, with the test cell 20 empty, the variable capacitor 92 may be adjusted until the two oscillator circuits 112 and 114 are in a balanced condition. It is well known that in such balanced condition the minimum amount of current, will flow in the common loop therebetween resulting in a minimum "meter" reading, or "null". The prior art apparatus in fact employed an ammeter to indicate this balanced or "null" condition. Accordingly, the test cell 20 may then be filled with the sample of material, whereupon the variable capacitor 92 is again adjusted to obtain a second null or minimum "meter" reading in the same fashion. Since the two capacitances (test cell 20 and variable capacitor 92) are in parallel, it will be recognized that the amount of capacitance removed from the circuit by re-adjusting the variable capacitor 92 is equal to the capacitance added to the circuit by the introduction of the sample into the test cell 20.

In the prior art apparatus, suitable charts or tables were provided for each material, whereby the operator could convert a reading from a graduated dial associated with a variable capacitor similar to capacitor 92 to a moisture content reading for the material being tested. Hence, not only may the relative position of the variable capacitor be readily equated with the capacitance thereof, but importantly, the change in position is indicative of the change in capacitance which occurs upon re-adjustment of the capacitor to cancel out the capacitance added by the introduction of the sample.

Accordingly, it was important in the prior art apparatus to accurately center or "zero" the capacitor with respect to its associated dial between readings. In this regard, it was equally important that the empty cell or calibration reading always be taken at exactly the same dial reading and hence capacitor position. Accordingly, the prior art arrangement provided an additional trimmer capacitor and a calibration procedure for this purpose. Moreover, the charts were based upon readings taken at a given reference temperature, whereby the temperature of the sample had to be separately measured and additional temperature correction tables referred to as well. As previously mentioned, the prior art device also utilized vacuum tube circuits for the reference and test cell oscillators and a microammeter for determining the null point at which the reading from the variable capacitor dial was to be recorded.

It will be appreciated from the foregoing description of the prior art that the meter, the dial markings and finally selecting and reading the charts in all instances presented problems in obtaining accurate measurements. Moreover, with increasing percents moisture and increasing capacitance, the sharpness or width of the null point is known to increase somewhat, such that an operator might experience some difficulty in determining the exact "null" point from observing the meter alone. Additionally, the degree of resolution obtainable by a manually adjusted dial and associated indicia was limited.

Advantageously, and referring again to FIG. 7, the present invention solves many of the foregoing problems of the prior art device. Initially, it will be seen that the reference oscillator circuit 112 and test cell oscillator circuit 114 comprise solid-state circuits. In this regard, both oscillators use FET components 116, 118, each of which preferably comprises an RCA type 40819 dual-gate MOSFET. The reference oscillator is provided with a crystal element 120 to further enhance and promote stability of the reference frequency signal provided thereby. Both oscillator circuits 112 and 114 further advantageously include automatic gain control (AGC) circuits 122 and 124, each of which comprises a pickup coil 126, a peak detector comprising transistor 128 and related components and an error amplifier 130. (The like components with respect to the circuit 122 are designated by like reference numerals with subscript a.) Preferably the error amplifiers 130 each comprise ½ of a dual operational amplifier of the type generally designated TL072, low-noise JFET input OP AMP.

The output of each error amplifier 130 modulates the transconductance of its associated FET 116, 118 by varying the voltage at the gate 2 (G2) electrode thereof. Also coupled at the respective gate electrodes (G1 and G2) of respective FET's 116 and 118 are additional coils 132, 134, (132a, 134a). These coils together with the previously mentioned pickup coils 126 (126a) are realized in the form of a pair of similar inductor elements, wound on respective common cores. Accordingly, each of these elements comprises a generally variably coupled inductance between respective windings 132, 134 on the one hand, and pickups 126 on the other hand and preferably a movable core piece 136 (136a) is provided to fine tune or otherwise adjust these respective inductors. Additionally, the coils 132 and 132a are coupled by way of suitable RC networks to a positive supply. Suitable RF shielding is also provided for the foregoing components as indicated by the dashed lines surrounding the circuits 112 and 114.

Coupling between the two oscillator circuits is defined by a diode 140 and series-coupled resistor 142 extending between pickup coil 126a and pickup coil 126. Hence the output or "null" voltage is developed across an output or load resistor 144. While such FET oscillators are known to present higher harmonic distortion than the vacuum tube-type oscillators which they replace, as mentioned above, this can also be minimized by constraining the drain-to-source voltage swings thereof. This is done by provision of the AGC loops as described above.

Moreover, it is believed that the provision of such AGC loops further allows substitution of a new FET, if necessary for either of the FET's 116 and 118 without experiencing problems stemming from different characteristics from one component to another. In contrast, the vacuum tube oscillators referred to above suffer in that their output voltages in the pickup links are affected by the transconductance of the tubes, whereby replacing one of the tubes may throw the circuit seriously out of balance such that a good null is no longer obtainable. Accordingly, the above-described FET-based oscillator circuit is advantageous in this regard as well.

Preferably, the peak-to-peak voltage at pickup coil 126a is at all times held by the illustrated circuits somewhat higher than the peak-to-peak (p-p) voltage at the pickup coil 126. In the illustrated embodiment, the voltages maintained at these elements are on the order of 3.4 V p-p and 3.0 V p-p respectively. This difference assures that the reference oscillator runs at a slightly higher amplitude at all times, in turn assuring that the "null" voltage developed across output resistor 144 is slightly positive at all times. Advantageously, this permits this voltage to be fed to a ground-referenced analog-to-digital (A/D) converter, as will presently be seen. In this regard, output resistor 144 is coupled by way of a suitable inductor 146 to the non-inverting input of a first operational amplifier (op amp) 148 (e.g., TL071). This first op amp 148 feeds a second amplifier stage 150 (e.g., LF398) whose output feeds the previously-mentioned A/D converter by way of an output line 152. Additionally, a DC blocking capacitor 154 provided in the base circuit of the transistor 128 serves to block the DC component of the null voltage at the base electrode of the transistor 128.

Referring to the lower left hand portion of FIG. 7, relays K1 and K2 and the associated like-designated coils respond to control signals at like designated inputs from a control circuit to be described later. These relays switch into circuit a pair of reference standardization networks 156 and 158. Preferably, one of these networks presents a relatively high capacitance and the other a relatively low capacitance, so as to perform an automatic self-check procedure each time the instrument is utilized. That is, as will presently be described, the known values of these reference networks are stored in a memory unit, whereby readings taken thereof may be compared with the known, stored value to assure proper functioning of the unit. An additional relay K3 shorts the gate 1 (G1) electrode of FET 118 to ground to protect the FET against damage from electrostatic discharge. This last relay K3 is preferably automatically held in closed condition when the unit is not in use to provide such protection. The K3 input also feeds a control point 155 at the emitter electrode of trannsistor 128.

Referring briefly to FIG. 8, the temperature sensor or sensing element 54 previously described with reference to FIGS. 1-4 and a related circuit are illustrated in circuit schematic form. Preferably sensor 54 comprises a temperature variable element of the type generally designated A0537KH. The pin numbers indicated in the circuit diagram of FIG. 8 correspond to the standard pin numbers of this component. The output signal of the temperature sensor 54 corresponding to the temperature sensed thereby is delivered to the control circuit of FIGS. 9A and 9B by way of an output terminal 160. Additionally, a solenoid activated signal (SOL.ACT.) feeds into the circuit at an input 162 while a dump cell signal (DUMP) feeds the circuit at an input 164. These signals relate to the automated operation of the test apparatus or unit of the invention as will next be described with reference to FIGS. 9A and 9B. A suitable regulated power supply 166 is also provided. Preferably, the foregoing circuit is mounted to a suitable printed circuit card (not shown here or in FIGS. 1-5) mounted in housing 52. Hence, the D.C. voltage and control lines 162 and 164 may be fed out to the solenoid 50 from this circuit board.

Figure 9A:
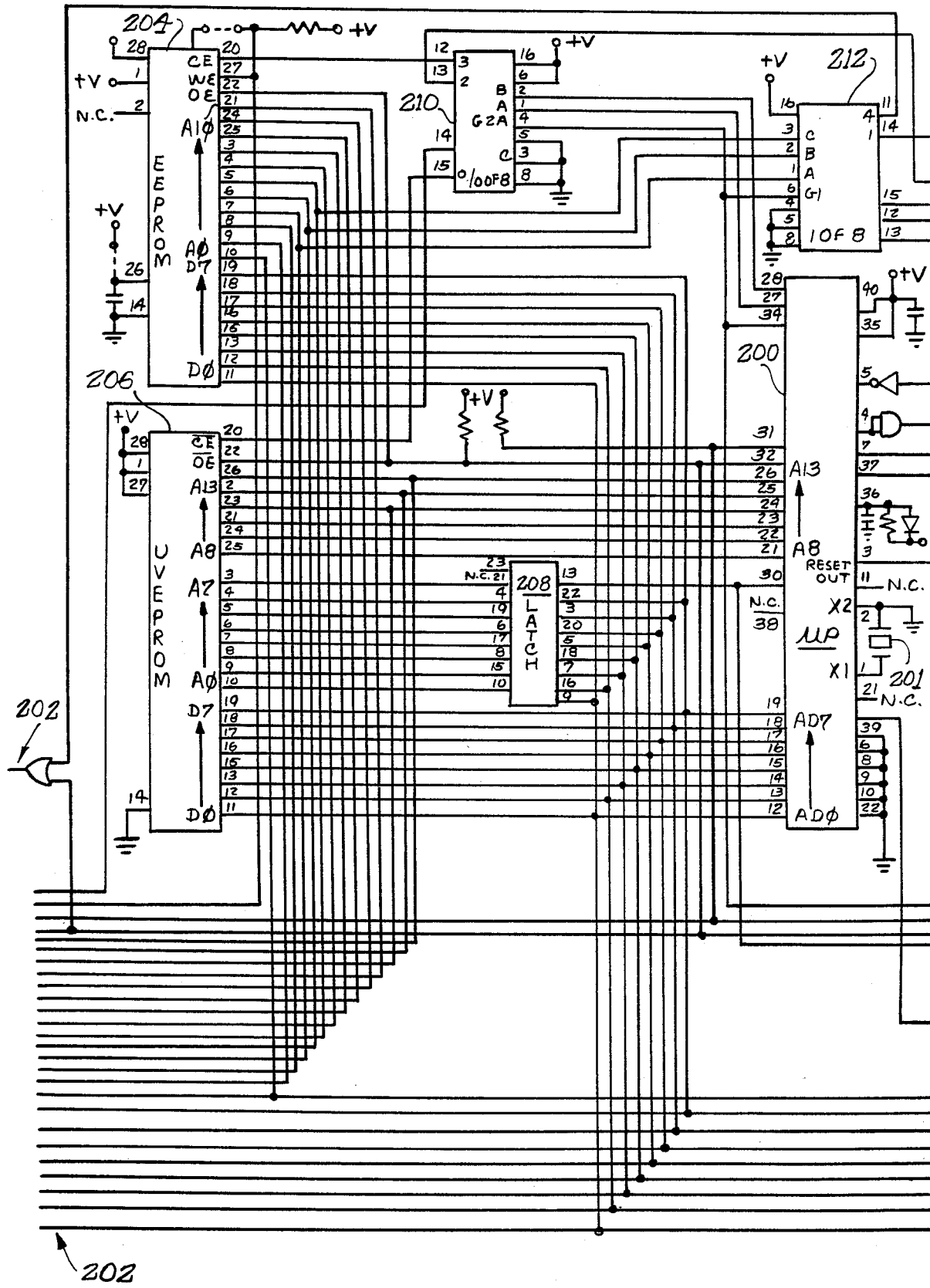

Referring now to FIGS. 9A and 9B, in accordance with a preferred form of the invention, a digital computer or microprocessor-based control circuit is utilized to perform the sequence of temperature measurement and delivery of the sample from the dump cell 30 to the test cell 20 as described above with reference to FIGS. 1-5. Moreover, this control circuit also controls operation of the stepping motor of FIG. 6, as previously described, so as to obtain "half" steps thereof, and to thereby obtain 4800 steps per 360 degrees revolution of the variable capacitor 92 as previously mentioned.

Advantageously, the use of the digital computer circuit of FIGS. 9A and 9B greatly facilitates operation of the aforementioned stepping motor to resolve the position of the variable capacitor with great accuracy. That is, the 4800 steps or positions per revolution, as previously mentioned, are readily counted during rotation of the motor, whereby the position of the capacitor at any time can be determined.

In this regard, a microprocessor 200 (FIG. 9A) is preferably of the type generally designated 8085AH, for example, as manufactured by intel. The various pins and their functional designations of the microprocessor are here designated in standard form and include an 8-bit data bus designated generally AD0-AD7. A 4-megahertz crystal 201 is provided at suitable crystal input terminals X1, X2 in conventional fashion. The previously mentioned plug-in module 82 preferably includes a solid-state memory component of the type generally designated 2732, which is a 4K by 8 EEPROM. The respective leads from this module are arranged to interconnect with terminals 202 at the lower right-hand side of FIG. 9A.

Additional "on-board" memory for the processor 200 is provided in a pair of memories 204, 206. In the illustrated embodiment, memory 204 comprises a 2K by 8 EEPROM of the type generally designated 2817, although a 2816 type may also be utilized. The memory 206 preferably comprises an ultraviolet erasable PROM (UVEPROM) of the type generally designated 2764 (8K by 8), however, a similar 27128, (16K by 8) unit may also be utilized. A suitable latch, preferably of the type designated 8212 as indicated at 208 interconnects a number of address lines of plug-in module-receiving terminals 202 as well as for memories 204 and 206 to be addressed from the microprocessor 200. Additional such memory address lines are coupled directly to corresponding lines of the processor as indicated by reference characters. Chip selection, that is, for selecting one of the memories 204 or 206, or the memory included in plug-in module 82 is provided in the form of a 1 of 8 decoder/demultiplexer 210 which in the illustrated embodiment may comprise a component of the type generally designated 74LS138. A second similar decoder demultiplexer 212 is provided for selecting one of the components of FIG. 9B the display 14, or the controls 16-19 (see FIG. 1) for input/output with the processor 200.

Referring now to FIG. 9B, the previously mentioned analog-to-digital conversion of the output signal of the circuit of FIG. 7 (on line 152 thereof) is accomplished by A to D converter 220 (A/D). In this regard, it will be remembered that the converter is ground referenced, whereby the line 152 feeds the like-referenced line of FIG. 9B and the negative voltage input line of the A/D converter 220 is tied to circuit ground. An additional peripheral comprises an input/output component 222 which in the illustrated embodiment preferably comprises a timer/RAM/I/O component of the type generally designated 8155 and as here designated in simplified form as "I/O".

The temperature output line 160 of the temperature circuit of FIG. 8 feeds the like designated line 160 (TEMP) of the I/O 222. Additional input/output lines are indicated in functional terminology in FIG. 9B. These include lines for controlling data transfer from plug-in module 82 as well as a HOLD control line from the circuit of FIG. 7. The solenoid activated (SOL.ACT.) line mentioned above with reference to the temperature circuit of FIG. 8 as well as suitable inputs from the dump cell position sensor switches 62, 64 (DUMP UP and DUMP DN) previously mentioned are also input to the I/O 222 with suitable intervening input circuitry. Outputs from the I/O 222 are fed through a suitable high current driver component 224 and include a control signal (DUMP) to release the doors of the dump cell to introduce the sample into the sample cell as previously described.

Additional outputs include lines designated K1, K2 and K3 for energizing the like-designated solenoids or relays of the circuit of FIG. 7. The remaining outputs designated generally by reference numeral 226 are coupled in predetermined fashion to the stepper or stepping motor 104 to achieve half-stepping thereof by intermittently energizing the four poles thereof in predetermined sequence as previously mentioned. This sequence is controlled by the processor 200 in accordance with suitable programmed instructions carried in memory 204 and/or 206. Additional inputs and outputs designated generally 228 are coupled to the control elements 16-19 and to the display 14 described above with reference to FIG. 3. These latter display driver outputs 228 preferably are fed out of the I/O 222 by way of a suitable bi-directional buss driver 230, which in the illustrated embodiment comprises an integrated circuit component of the type generally designated 74LS245. Preferably, the display 14 comprises a liquid crystal display (LCD), and is provided with suitable decoder and driver circuitry (not shown).

In operation, the microprocessor 200 and associated memory components 204 and/or 206 are programmed to carry out a predetermined sequence of automated operation with respect to the test apparatus shown and described earlier in FIGS. 1-6. Initially, upon powering up the unit, the digital computer performs an "orienting" operation, driving the stepping motor to locate a readily-refindable base or reference point with respect to the position of variable capacitor 92. In this regard, it has been found that with the test cell 20 empty, the null points, that is the positions of the variable capacitor at which the oscillator circuits of FIG. 7 balance, are substantially equidistant from the point at which respective movable plates 96 and fixed plates 94 are substantially in a "fully meshed" condition. Accordingly, this "fully meshed" position may be utilized as a base, reference or "step 1" point in determining the other positions of the stepping motor and gear drive assembly, which will be remembered to be 4800 possible incremental positions about 360 degrees of rotation thereof.

A surprisingly high degree of resolution of capacitor position and hence value, and by extension, of moisture contents of materials being measured is obtainable by the invention. That is, the processor 200 is capable, in view of the A to D conversion provided by A/D circuit 220 of counting and registering the steps of rotation of motor 104, and hence determining the relative position of the variable capacitor 92 at all times, based upon this "step 1" or "fully meshed" reference or base position. In practice, this base position may be recomputed initially upon powering up of the unit to confirm the proper functioning thereof, by comparison with data regarding the base position stored in memory.

Accordingly, this base or "fully meshed" position may be utilized so that the processor in effect counts the incremental steps occurring between this base position and any other relative setting or position of variable capacitor 92, so as to obtain a highly accurate and repeatable reading of relative positions thereof and therefore of the change in capacitance values. It will be remembered that it is the change in the capacitance value between that obtained with the empty test cell and that obtained with the test cell filled with sample that is indicative of the capacitance value and hence moisture content of the sample.

In conjunction with each test initiated, the relays K1 and K2 are also selectively energized in the proper sequence to obtain readings of the values of the associated standardized capacitance networks. These readings are then also compared with readings previously stored in the memory circuits of FIG. 9A to reconfirm proper operation of the unit and its circuits. In practice, a single 360 degree revolution of the stepping motor 104 may be utilized, under control of the processor 200 with proper switching, in sequence, of the standardizing networks and reading of empty test cell null points. Accordingly, a single revolution is controlled in proper sequence to achieve this initial setting up, calibration or verification of proper operation of the unit and circuits of the invention, all in an automated fashion.

It will be recognized in this regard that each measurement, that is, of the empty test cell, of the relatively high standardized network and of the relatively low capacitance standardized network will be again capable of testing and confirmation at a "mirror image" point defined by the relative intermeshing of the plates of variable capacitor 92. Accordingly, each reading is in effect taken twice per 360 degrees revolution of movable or rotatable plates 92, and this may also be utilized to reconfirm the proper operation of the unit and circuits of the invention.

At the same time, the foregoing setup procedures are automatically taking place, the temperature of a sample of material pre-weighed and introduced to dump cell 30 as previously described is measured by temperature sensor 54. This information is also fed to the processor 200 and held in memory for later use in automatically adding any necessary temperature corrections to the moisture measurement.

Upon completion of the foregoing operations, the solenoid 50 is automatically actuated to allow the doors 34, 36 to drop and introduce the sample of material into test cell 20. Thereupon, the motor 104 is again actuated in the same fashion to rotate the movable plates of variable capacitor 92 through another 360 degrees, carefully noting the exact ones of the 4800 steps per revolution where the "null" point occurs. From this information, coupled with the information as to the particular material under test (that is, its characteristic capacitance versus moisture) as carried in the plug-in unit 82, the processor 200 can readily calculate the moisture content of the sample. Additionally, a temperature correction, as previously mentioned, is also utilized in arriving at moisture content.

Advantageously, the fact that exact linearity is not obtainable in a variable capacitor may be readily compensated for by the novel microprocessor components of the invention. Moreover, differences or variations from one unit to another may readily be compensated for. In this regard, the memory components 204 and/or 206 may readily be programmed with information obtained during factory testing and calibration of each unit so as to provide automatic corrections for any non-linearities or other variations obtained during operation of the unit. Briefly, this is done by substituting high-accuracy standardized capacitance components for the test cell 20, obtaining readings on the unit, and putting into memory any necessary correction factors in view of the variance of these readings from the known values of the test standards. This process is often referred to as "linearization" of the unit.

In order to provide a full description of one specific embodiment of the invention, the following pages contain a listing of an exemplary program for the microprocessor 200.

While the invention has been illustrated and described herein with reference to specific embodiments, the invention is not limited thereto. Those skilled in the art may devise various changes, alternatives and modifications. Such changes, alternatives and modifications are included in the invention insofar as they fall within the spirit and scope of the appended claims.

```
ISIS-II 8080/8085 MACRO ASSEMBLER, V4.1        MODULE   PAGE   1
MOTOMCO 919 AUTO INTERRUPT VECTOR

LOC  OBJ         LINE       SOURCE STATEMENT
                                               © 1983 DICKEY-john Corporation--.
                     1   $ TITLE('MOTOMCO 919 AUTO INTERRUPT VECTOR')
                     2   $ DEBUG
                     3   $ MOD85
                     4
                     5           EXTRN   INT
                     6 ;
    003C             7           ORG     3CH
                     8 ;
    003C C30000  E   9           JMP     INT
                     10 ;
                     11          END

PUBLIC SYMBOLS

EXTERNAL SYMBOLS
INT   E 0000

USER SYMBOLS
INT   E 0000

ASSEMBLY COMPLETE,  NO ERRORS

ISIS-II PL/M-80 V4.0 COMPILATION OF MODULE MAIN
OBJECT MODULE PLACED IN :F1:MAIN.OBJ
COMPILER INVOKED BY:  PLM80 :F1:MAIN.PLM $ TITLE('MOTOMCO 919 AUTOMATIC MAIN ROUTINE')
            $ DATE(28 MAY 83)
            $ DEBUG
            $ NOINTVECTOR
                                               © 1983 DICKEY-john Corporation--.
    1           MAIN: DO;

2    1         DECLARE BUSY LITERALLY '0';
    3    1         DECLARE CHART$DATA$DISPLAYED LITERALLY '3';
    4    1         DECLARE ERROR$DETECTED LITERALLY '6';
    5    1         DECLARE FALSE LITERALLY '0';
    6    1         DECLARE LONG LITERALLY '500';
    7    1         DECLARE MOISTURE$DISPLAYED LITERALLY '4';
    8    1         DECLARE READY$CHART$DATA$SELECTED LITERALLY '1';
    9    1         DECLARE READY$GRAIN$SELECTED LITERALLY '2';
    10   1         DECLARE SHORT LITERALLY '100';
    11   1         DECLARE TEST$KEY$DATA LITERALLY '20H';
```

```
12   1      DECLARE TEST$NETWORK$DATA$DISPLAYED LITERALLY '5';
13   1      DECLARE TRUE LITERALLY 'OFFH';

14   1      DECLARE COLLECTING$DATA BYTE PUBLIC;
15   1      DECLARE COUNTING BYTE PUBLIC;
16   1      DECLARE DATA$AVAILABLE BYTE PUBLIC;
17   1      DECLARE DATA$COLLECTION$COMPLETE BYTE PUBLIC;
18   1      DECLARE DATA$COLLECTION$ERROR BYTE PUBLIC;
19   1      DECLARE DATA$PENDING BYTE PUBLIC;
20   1      DECLARE DUMP$CELL$DOWN BYTE PUBLIC;
21   1      DECLARE DUMP$CELL$UP BYTE;
22   1      DECLARE ERROR BYTE PUBLIC;
23   1      DECLARE FAHRENHEIT BYTE PUBLIC;
24   1      DECLARE MEASURING$TEMPERATURE BYTE PUBLIC;
25   1      DECLARE RESET$PENDING BYTE PUBLIC;
26   1      DECLARE SEEK$HOME BYTE;
27   1      DECLARE SEEKING$MINIMUM BYTE PUBLIC;
28   1      DECLARE SETTLING BYTE PUBLIC;
29   1      DECLARE TEST$KEY$DOWN BYTE;
30   1      DECLARE VALID$KEY$DOWN BYTE;

31   1      DECLARE ABSOLUTE$MINIMUM BYTE PUBLIC;
32   1      DECLARE AVERAGE BYTE PUBLIC;
33   1      DECLARE BEEP$TIMER ADDRESS PUBLIC;
34   1      DECLARE BUFFER(6) BYTE PUBLIC;
35   1      DECLARE CALIBRATION$NUMBER BYTE PUBLIC;
36   1      DECLARE DATA$POINT(8) BYTE PUBLIC;
37   1      DECLARE EMPTY$CELL$DATA(6) ADDRESS PUBLIC;
38   1      DECLARE FULL$CELL$DATA(2) ADDRESS PUBLIC;
39   1      DECLARE HOME ADDRESS PUBLIC;
40   1      DECLARE I ADDRESS PUBLIC;
41   1      DECLARE INDEX BYTE PUBLIC;
42   1      DECLARE J ADDRESS PUBLIC;
43   1      DECLARE K BYTE PUBLIC;
44   1      DECLARE KEY$NUMBER BYTE;
45   1      DECLARE MACHINE$STATE BYTE PUBLIC;
46   1      DECLARE MINIMUM BYTE PUBLIC;
47   1      DECLARE MOTOR$STEP BYTE PUBLIC;
48   1      DECLARE NEW$KEY$DATA BYTE;
49   1      DECLARE POINTER BYTE PUBLIC;
50   1      DECLARE PORT$1$DATA BYTE PUBLIC;
51   1      DECLARE PORT$3$DATA BYTE PUBLIC;
52   1      DECLARE READING BYTE PUBLIC;
53   1      DECLARE REGISTER$1(5) BYTE PUBLIC;
54   1      DECLARE REGISTER$2(5) BYTE PUBLIC;
55   1      DECLARE SAMPLE$NUMBER ADDRESS PUBLIC;
56   1      DECLARE SETTLE$TIMER ADDRESS PUBLIC;
57   1      DECLARE SUM ADDRESS PUBLIC;
58   1      DECLARE TEMPERATURE$DATA(6) BYTE;
59   1      DECLARE TEMPERATURE$INDEX BYTE PUBLIC;
60   1      DECLARE TEMPERATURE$TIMER ADDRESS PUBLIC;
61   1      DECLARE VALID$KEY$DATA BYTE;

62   1      DECLARE A$EMPTY$CELL      ADDRESS PUBLIC AT (.EMPTY$CELL$DATA(0));
63   1      DECLARE A$TEST$NETWORK$1 ADDRESS PUBLIC AT (.EMPTY$CELL$DATA(1));
64   1      DECLARE A$TEST$NETWORK$2 ADDRESS PUBLIC AT (.EMPTY$CELL$DATA(2));
65   1      DECLARE B$TEST$NETWORK$2 ADDRESS PUBLIC AT (.EMPTY$CELL$DATA(3));
66   1      DECLARE B$TEST$NETWORK$1 ADDRESS PUBLIC AT (.EMPTY$CELL$DATA(4));
67   1      DECLARE B$EMPTY$CELL      ADDRESS PUBLIC AT (.EMPTY$CELL$DATA(5));
```

```
68   1       DECLARE A$FULL$CELL ADDRESS PUBLIC AT (.FULL$CELL$DATA(0));
69   1       DECLARE B$FULL$CELL ADDRESS PUBLIC AT (.FULL$CELL$DATA(1));

70   1       DECLARE KEY$TABLE(5) BYTE DATA(04H,02H,80H,40H,10H);
71   1       DECLARE NETWORK$TABLE(6) BYTE PUBLIC DATA(0,20H,10H,10H,20H,0);
72   1       DECLARE STEP$SEQUENCE(8) BYTE PUBLIC DATA(0AH,8,9,1,5,4,6,2);

73   1       DECLARE CHECKING(8) BYTE PUBLIC DATA('CHECKING');
74   1       DECLARE REMOVE(8)   BYTE PUBLIC DATA(' REMOVE ');
75   1       DECLARE REPLACE(8)  BYTE        DATA('REPLACE ');
76   1       DECLARE SELECT(8)   BYTE        DATA(' SELECT ');
77   1       DECLARE TESTING(8)  BYTE PUBLIC DATA('TESTING ');

78   1       DECLARE CODE$MESSAGE(16)           BYTE PUBLIC DATA('CODE           ');
79   1       DECLARE CELL$MOVED$MESSAGE(16)     BYTE        DATA('   CELL MOVED  ');
80   1       DECLARE CHART$DATA$MESSAGE(16)     BYTE        DATA('   CHART DATA  ');
81   1       DECLARE LIMIT$EXCEEDED$MESSAGE(16) BYTE PUBLIC DATA(' LIMIT EXCEEDED ');
82   1       DECLARE PLEASE$WAIT$MESSAGE(16)    BYTE PUBLIC DATA('  PLEASE WAIT  ');
83   1       DECLARE TEST$NETWORK$1$MESSAGE(16) BYTE        DATA(' TEST NETWORK 1 ');
84   1       DECLARE TEST$NETWORK$2$MESSAGE(16) BYTE        DATA(' TEST NETWORK 2 ');

85   1       DECLARE CONSTANT$P500000EN001(5) BYTE PUBLIC DATA(0,0,50H,0FFH,0);
86   1       DECLARE CONSTANT$N500000EP000(5) BYTE PUBLIC DATA(0,0,50H,0,80H);
87   1       DECLARE CONSTANT$P500000EP000(5) BYTE PUBLIC DATA(0,0,50H,0,0);
88   1       DECLARE CONSTANT$P200000EP001(5) BYTE PUBLIC DATA(0,0,20H,1,0);
9    1       DECLARE CONSTANT$P500000EP001(5) BYTE PUBLIC DATA(0,0,50H,1,0);

90   1       BEEP: PROCEDURE (BEEP$TIME) EXTERNAL;
91   2           DECLARE BEEP$TIME ADDRESS;
92   2       END;

93   1       BEEPER$ON: PROCEDURE BYTE EXTERNAL;
94   2       END;

95   1       BOTTOM$DISPLAY: PROCEDURE (BOTTOM$POINTER) EXTERNAL;
96   2           DECLARE BOTTOM$POINTER ADDRESS;
97   2       END;

98   1       CALCULATE$CHART$DATA: PROCEDURE EXTERNAL;
99   2       END;

100  1       CALCULATE$TEST$NETWORK$1$DATA: PROCEDURE EXTERNAL;
101  2       END;

102  1       CALCULATE$TEST$NETWORK$2$DATA: PROCEDURE EXTERNAL;
103  2       END;

104  1       CELL$DOWN: PROCEDURE BYTE EXTERNAL;
105  2       END;
```

```
106   1      CELL$UP: PROCEDURE BYTE EXTERNAL;
107   2      END;

108   1      CLEAR: PROCEDURE EXTERNAL;
109   2      END;

110   1      CLEAR$BOTTOM$DISPLAY: PROCEDURE EXTERNAL;
111   2      END;

112   1      CLEAR$TOP$DISPLAY: PROCEDURE EXTERNAL;
113   2      END;

4   1      DATA$COLLECTION: PROCEDURE EXTERNAL;
115   2      END;
116   1      DATA$TERMINAL$READY: PROCEDURE BYTE EXTERNAL;
117   2      END;

118   1      DISPLAY$GRAIN$NAME: PROCEDURE EXTERNAL;
119   2      END;

120   1      DISPLAY$SAMPLE$WEIGHT: PROCEDURE EXTERNAL;
121   2      END;

122   1      DISPLAY$X: PROCEDURE EXTERNAL;
123   2      END;

124   1      EMPTY$CELL: PROCEDURE EXTERNAL;
125   2      END;

126   1      GO$HOME: PROCEDURE EXTERNAL;
127   2      END;

128   1      KEY$DATA: PROCEDURE BYTE EXTERNAL;
129   2      END;

30   1      LOAD: PROCEDURE (POINTER) EXTERNAL;
131   2         DECLARE POINTER ADDRESS;
132   2      END;

133   1      OUTPUT$CHART$DATA: PROCEDURE EXTERNAL;
134   2      END;

135   1      OUTPUT$DISPLAY$CONTROL: PROCEDURE (DISPLAY$CONTROL) EXTERNAL;
136   2         DECLARE DISPLAY$CONTROL BYTE;
137   2      END;

138   1      OUTPUT$EMPTY$CELL$DATA: PROCEDURE EXTERNAL;
139   2      END;
```

```
140  1        OUTPUT$FULL$CELL$DATA: PROCEDURE EXTERNAL;
141  2        END;

142  1        OUTPUT$TEMPERATURE$DATA: PROCEDURE EXTERNAL;
143  2        END;

144  1        PULSE$DOOR$SOLENOID: PROCEDURE EXTERNAL;
145  2        END;
146  1        SET$CELL$SHORT: PROCEDURE EXTERNAL;
147  2        END;

148  1        S$MASK: PROCEDURE (MASK) EXTERNAL;
149  2          DECLARE MASK BYTE;
150  2        END;

151  1        STEP$MOTOR: PROCEDURE EXTERNAL;
152  2        END;

153  1        STORE: PROCEDURE (POINTER) EXTERNAL;
154  2          DECLARE POINTER ADDRESS;
155  2        END;

156  1        TIMER: PROCEDURE (TIME$COUNT) EXTERNAL;
157  2          DECLARE TIME$COUNT ADDRESS;
158  2        END;

159  1        TOP$DISPLAY: PROCEDURE (TOP$POINTER) EXTERNAL;
160  2          DECLARE TOP$POINTER ADDRESS;
161  2        END;

162  1        INT: PROCEDURE INTERRUPT 7 PUBLIC;
163  2          IF COLLECTING$DATA THEN DO;
165  3            IF DATA$PENDING THEN DO;
167  4              READING = INPUT(8);
168  4              DATA$PENDING = FALSE;
169  4              DATA$AVAILABLE = TRUE;
170  4              PORT$3$DATA = (PORT$3$DATA AND 0FEH);
171  4              OUTPUT(3) = PORT$3$DATA;
172  4            END;
173  3            ELSE DO;
174  4              PORT$3$DATA = (PORT$3$DATA OR 1);
175  4              OUTPUT(3) = PORT$3$DATA;
176  4              OUTPUT(8) = 0;
177  4              DATA$PENDING = TRUE;
178  4              CALL STEP$MOTOR;
179  4            END;
180  3          END;
181  2          IF MEASURING$TEMPERATURE THEN DO;
183  3            TEMPERATURE$TIMER = TEMPERATURE$TIMER - 1;
184  3            IF TEMPERATURE$TIMER = 0 THEN DO;
186  4              IF COUNTING THEN DO;
188  5                OUTPUT(0) = 4DH;
189  5                COUNTING = FALSE;
```

```
190  5          TEMPERATURE$DATA (TEMPERATURE$INDEX) = INPUT(4);
191  5          TEMPERATURE$INDEX = TEMPERATURE$INDEX + 1;
192  5          TEMPERATURE$DATA (TEMPERATURE$INDEX) = INPUT(5);
193  5          TEMPERATURE$INDEX = TEMPERATURE$INDEX + 1;
194  5          IF TEMPERATURE$INDEX < 5 THEN DO;
196  6             TEMPERATURE$TIMER = 5500;
197  6          END;
198  5          ELSE DO;
199  6             MEASURING$TEMPERATURE = FALSE;
200  6          END;
201  5        END;
202  4        ELSE DO;
203  5          OUTPUT(4) = 0FEH;
204  5          OUTPUT(5) = 03FH;
205  5          OUTPUT(0) = 0CDH;
206  5          COUNTING = TRUE;
207  5          TEMPERATURE$TIMER = 500;
208  5        END;
209  4      END;
210  3    END;
211  2    IF BEEPER$ON THEN DO;
213  3      BEEP$TIMER = BEEP$TIMER - 1;
214  3      IF BEEP$TIMER = 0 THEN DO;
216  4        PORT$3$DATA = (PORT$3$DATA AND 0FDH);
217  4        OUTPUT(3) = PORT$3$DATA;
218  4      END;
219  3    END;
220  2    IF DUMP$CELL$DOWN THEN DO;
222  3      IF NOT CELL$DOWN THEN DO;
224  4        DUMP$CELL$DOWN = FALSE;
225  4        IF COLLECTING$DATA THEN DO;
227  5          CALL SET$CELL$SHORT;
228  5          ERROR = TRUE;
229  5          CALL BOTTOM$DISPLAY (.CELL$MOVED$MESSAGE);
230  5        END;
231  4      END;
232  3    END;
233  2  END;

234  1  DISPLAY$CHART$DATA: PROCEDURE;
235  2    ;
236  2  END;

237  1  DISPLAY$CHART$NUMBER: PROCEDURE;
238  2    ;
239  2  END;

240  1  DISPLAY$SAMPLE$TEMPERATURE: PROCEDURE;
241  2    ;
242  2  END;

243  1  DUPLICATE$MOISTURE$PRINTOUT: PROCEDURE;
244  2    ;
245  2  END;
246  1  MEASURE$CHART$DATA: PROCEDURE;
247  2    CALL BEEP (SHORT);
248  2    CALL DATA$COLLECTION;
249  2    IF NOT ERROR THEN DO;
251  3      IF DATA$TERMINAL$READY THEN DO;
```

```
253  4          CALL OUTPUT$CHART$DATA;
254  4        END;
255  3        CALL CALCULATE$CHART$DATA;
256  3        IF NOT ERROR THEN DO;
258  4          CALL CLEAR$TOP$DISPLAY;
259  4          CALL DISPLAY$X;
260  4          MACHINE$STATE = CHART$DATA$DISPLAYED;
261  4        END;
262  3        CALL BEEP (LONG);
263  3      END;
264  2    END;

265  1    MEASURE$TEST$NETWORK$1: PROCEDURE;
266  2      CALL BEEP (SHORT);
267  2      RESET$PENDING = TRUE;
268  2      CALL TOP$DISPLAY (.TESTING);
269  2      CALL BOTTOM$DISPLAY (.TEST$NETWORK$1$MESSAGE);
270  2      CALL EMPTY$CELL;
271  2      IF NOT ERROR THEN DO;
273  3        CALL CALCULATE$TEST$NETWORK$1$DATA;
274  3        IF NOT ERROR THEN DO;
276  4          CALL CLEAR$TOP$DISPLAY;
277  4          CALL DISPLAY$X;
278  4          MACHINE$STATE = TEST$NETWORK$DATA$DISPLAYED;
279  4        END;
280  3        CALL BEEP (LONG);
281  3      END;
282  2    END;

283  1    MEASURE$TEST$NETWORK$2: PROCEDURE;
284  2      CALL BEEP (SHORT);
285  2      RESET$PENDING = TRUE;
286  2      CALL TOP$DISPLAY (.TESTING);
287  2      CALL BOTTOM$DISPLAY (.TEST$NETWORK$2$MESSAGE);
288  2      CALL EMPTY$CELL;
289  2      IF NOT ERROR THEN DO;
291  3        CALL CALCULATE$TEST$NETWORK$2$DATA;
292  3        IF NOT ERROR THEN DO;
294  4          CALL CLEAR$TOP$DISPLAY;
295  4          CALL DISPLAY$X;
296  4          MACHINE$STATE = TEST$NETWORK$DATA$DISPLAYED;
297  4        END;
298  3        CALL BEEP (LONG);
299  3      END;
300  2    END;

301  1    MEASURE$MOISTURE: PROCEDURE;
302  2      ;
303  2    END;

304  1    PRINT$EMPTY$CELL$DATA: PROCEDURE;
305  2      CALL BEEP (SHORT);
306  2      IF DATA$TERMINAL$READY THEN DO;
308  3        DO WHILE BEEPER$ON;
309  4        END;
310  3        CALL OUTPUT$EMPTY$CELL$DATA;
311  3      END;
312  2    END;
```

```
313  1     PRINT$FULL$CELL$DATA: PROCEDURE;
314  2       CALL BEEP (SHORT);
315  2       IF DATA$TERMINAL$READY THEN DO;
317  3         DO WHILE BEEPER$ON;
318  4         END;
319  3         CALL OUTPUT$FULL$CELL$DATA;
320  3       END;
321  2     END;

322  1     PRINT$TEMPERATURE$DATA: PROCEDURE;
323  2       CALL BEEP (SHORT);
324  2       IF DATA$TERMINAL$READY THEN DO;
326  3         DO WHILE BEEPER$ON;
327  4         END;
328  3         CALL OUTPUT$TEMPERATURE$DATA;
329  3       END;
330  2     END;

331  1     SCROLL$TOWARD$A: PROCEDURE;
332  2       SEEK$HOME = TRUE;
333  2     END;

334  1     SCROLL$TOWARD$Z: PROCEDURE;
335  2       ;
336  2     END;

337  1     OUTPUT(0) = 0DH;
338  1     OUTPUT(1) = 0AH;
339  1     OUTPUT(3) = 01H;
340  1     CALL OUTPUT$DISPLAY$CONTROL (30H);
341  1     CALL OUTPUT$DISPLAY$CONTROL (30H);
342  1     CALL OUTPUT$DISPLAY$CONTROL (30H);
343  1     CALL OUTPUT$DISPLAY$CONTROL (01H);
344  1     CALL OUTPUT$DISPLAY$CONTROL (06H);
345  1     CALL OUTPUT$DISPLAY$CONTROL (0CH);
346  1     CALL CLEAR;
347  1     RESET$PENDING = TRUE;
348  1     SEEK$HOME = TRUE;
349  1     CALL S$MASK (0DBH);
350  1     ENABLE;
351  1     DO WHILE 1;
352  2       IF RESET$PENDING THEN DO;
354  3         RESET$PENDING = FALSE;
355  3         CALL TOP$DISPLAY (.REMOVE);
356  3         DUMP$CELL$UP = FALSE;
357  3         DO WHILE NOT DUMP$CELL$UP;
358  4           DO WHILE NOT CELL$UP;
359  5           END;
360  4           CALL TIMER (500);
361  4           IF CELL$UP THEN DO;
363  5             DUMP$CELL$UP = TRUE;
364  5           END;
365  4         END;
366  3         CALL PULSE$DOOR$SOLENOID;
367  3         CALL TOP$DISPLAY (.REPLACE);
368  3         DO WHILE CELL$UP;
```

```
369  4        END;
370  3        DUMP$CELL$UP = FALSE;
371  3      END;
372  2      ELSE DO;
373  3        CALL TOP$DISPLAY (.REPLACE);
374  3      END;

375  2      DO WHILE NOT DUMP$CELL$DOWN;
376  3        IF CELL$DOWN THEN DO;
378  4          CALL TIMER (500);
379  4          IF CELL$DOWN THEN DO;
381  5            DUMP$CELL$DOWN = TRUE;
382  5          END;
383  4        END;
384  3        ELSE DO;
385  4          IF CELL$UP THEN DO;
387  5            CALL TIMER (500);
388  5            IF CELL$UP THEN DO;
390  6              CALL PULSE$DOOR$SOLENOID;
391  6              DO WHILE CELL$UP;
392  7              END;
393  6            END;
394  5          END;
395  4        END;
396  3      END;

397  2      IF NOT SEEK$HOME THEN DO;
399  3        IF CALIBRATION$NUMBER = 0 THEN DO;
401  4          CALL TOP$DISPLAY (.SELECT);
402  4          CALL BOTTOM$DISPLAY (.CHART$DATA$MESSAGE);
403  4          MACHINE$STATE = READY$CHART$DATA$SELECTED;
404  4        END;
405  3        ELSE DO;
406  4          CALL DISPLAY$SAMPLE$WEIGHT;
407  4          CALL DISPLAY$GRAIN$NAME;
408  4          MACHINE$STATE = READY$GRAIN$SELECTED;
409  4        END;
410  3      END;
411  2      DO WHILE DUMP$CELL$DOWN;
412  3        IF SEEK$HOME THEN DO;
414  4          CALL GO$HOME;
415  4          IF NOT ERROR THEN DO;
417  5            SEEK$HOME = FALSE;
418  5            IF CALIBRATION$NUMBER = 0 THEN DO;
420  6              CALL TOP$DISPLAY (.SELECT);
421  6              CALL BOTTOM$DISPLAY (.CHART$DATA$MESSAGE);
422  6              MACHINE$STATE = READY$CHART$DATA$SELECTED;
423  6            END;
424  5            ELSE DO;
425  6              CALL DISPLAY$SAMPLE$WEIGHT;
426  6              CALL DISPLAY$GRAIN$NAME;
427  6              MACHINE$STATE = READY$GRAIN$SELECTED;
428  6            END;
429  5          END;
430  4        END;
431  3        ELSE DO;
432  4          IF TEST$KEY$DOWN THEN DO;
434  5            IF (KEY$DATA AND TEST$KEY$DATA) <> TEST$KEY$DATA THEN DO;
436  6              TEST$KEY$DOWN = FALSE;
437  6            END;
438  5          END;
439  4          ELSE DO;
440  5            IF (KEY$DATA AND TEST$KEY$DATA) = TEST$KEY$DATA THEN DO;
```

```
442  6        TEST$KEY$DOWN = TRUE;
443  6        DO K = 1 TO 10;
444  7          IF (KEY$DATA AND TEST$KEY$DATA) <> TEST$KEY$DATA THEN DO;
446  8            TEST$KEY$DOWN = FALSE;
447  8          END;
448  7          HALT;
449  7        END;
450  6        IF TEST$KEY$DOWN THEN DO;
452  7          CALL BEEP (SHORT);
453  7        END;
454  6      END;
455  5    END;
456  4    IF VALID$KEY$DOWN THEN DO;
458  5      IF (KEY$DATA AND (NOT TEST$KEY$DATA)) <> VALID$KEY$DATA THEN DO;
460  6        VALID$KEY$DOWN = FALSE;
461  6      END;
462  5    END;
463  4    ELSE DO;
464  5      KEY$NUMBER = 0;
465  5      DO WHILE (NOT VALID$KEY$DOWN) AND (KEY$NUMBER < 5);
466  6        IF KEY$TABLE(KEY$NUMBER) = (KEY$DATA AND (NOT TEST$KEY$DATA)) THEN DO;
468  7          VALID$KEY$DATA = (KEY$DATA AND (NOT TEST$KEY$DATA));
469  7          VALID$KEY$DOWN = TRUE;
470  7        END;
471  6        ELSE DO;
472  7          KEY$NUMBER = KEY$NUMBER + 1;
473  7        END;
474  6      END;
475  5      IF VALID$KEY$DOWN THEN DO;
477  6        DO K = 1 TO 10;
478  7          IF (KEY$DATA AND (NOT TEST$KEY$DATA)) <> VALID$KEY$DATA THEN DO;
480  8            VALID$KEY$DOWN = FALSE;
481  8          END;
482  7          HALT;
483  7        END;
484  6        IF VALID$KEY$DOWN THEN DO;
486  7          DO CASE MACHINE$STATE;
487  8            ;
488  8            DO;
489  9              IF TEST$KEY$DOWN THEN DO;
491  10               DO CASE KEY$NUMBER;
492  11                 ;
493  11                 ;
494  11                 CALL MEASURE$TEST$NETWORK$1;
495  11                 CALL MEASURE$TEST$NETWORK$2;
496  11                 ;
497  11               END;
498  10             END;
499  9              ELSE DO;
500  10               DO CASE KEY$NUMBER;
501  11                 CALL SCROLL$TOWARD$A;
502  11                 CALL SCROLL$TOWARD$Z;
503  11                 ;
504  11                 CALL MEASURE$CHART$DATA;
505  11                 ;
506  11               END;
507  10             END;
508  9              END;
509  8            DO;
510  9              IF TEST$KEY$DOWN THEN DO;
512  10               DO CASE KEY$NUMBER;
513  11                 CALL DISPLAY$CHART$NUMBER;
514  11                 CALL DISPLAY$CHART$NUMBER;
```

```
515  11              CALL MEASURE$TEST$NETWORK$1;
516  11              CALL MEASURE$TEST$NETWORK$2;
517  11              ;
518  11            END;
519  10          END;
520   9        ELSE DO;
521  10          DO CASE KEY$NUMBER;
522  11              CALL SCROLL$TOWARD$A;
523  11              CALL SCROLL$TOWARD$Z;
524  11              CALL MEASURE$MOISTURE;
525  11              ;
526  11              ;
527  11            END;
528  10          END;
529   9        END;
530   8      DO;
531   9        IF TEST$KEY$DOWN THEN DO;
533  10          DO CASE KEY$NUMBER;
534  11              ;
535  11              ;
536  11              CALL PRINT$FULL$CELL$DATA;
537  11              CALL PRINT$EMPTY$CELL$DATA;
538  11              CALL PRINT$TEMPERATURE$DATA;
539  11            END;
540  10          END;
541   9        ELSE DO;
542  10          DO CASE KEY$NUMBER;
543  11              ;
544  11              ;
545  11              ;
546  11              ;
547  11              CALL DISPLAY$SAMPLE$TEMPERATURE;
548  11            END;
549  10          END;
550   9        END;
551   8      DO;
552   9        IF TEST$KEY$DOWN THEN DO;
554  10          DO CASE KEY$NUMBER;
555  11              CALL DISPLAY$CHART$NUMBER;
556  11              CALL DISPLAY$CHART$NUMBER;
557  11              CALL PRINT$FULL$CELL$DATA;
558  11              CALL PRINT$EMPTY$CELL$DATA;
559  11              CALL PRINT$TEMPERATURE$DATA;
560  11            END;
561  10          END;
562   9        ELSE DO;
563  10          DO CASE KEY$NUMBER;
564  11              ;
565  11              ;
566  11              CALL DUPLICATE$MOISTURE$PRINTOUT;
567  11              CALL DISPLAY$CHART$DATA;
568  11              CALL DISPLAY$SAMPLE$TEMPERATURE;
569  11            END;
570  10          END;
571   9        END;
572   8      DO;
573   9        IF TEST$KEY$DOWN THEN DO;
575  10          DO CASE KEY$NUMBER;
576  11              ;
577  11              ;
578  11              CALL PRINT$EMPTY$CELL$DATA;
579  11              ;
580  11              ;
```

```
581  11                    END;
582  10                   END;
583   9                  END;
584   8                  DO;
585   9                   IF TEST$KEY$DOWN THEN DO;
587  10                    DO CASE KEY$NUMBER;
588  11                     ;
589  11                     ;
590  11                     CALL PRINT$FULL$CELL$DATA;
591  11                     CALL PRINT$EMPTY$CELL$DATA;
592  11                     CALL PRINT$TEMPERATURE$DATA;
593  11                    END;
594  10                   END;
595   9                  END;
596   8                 END;
597   7                 IF ERROR THEN DO;
549   8                   MACHINE$STATE = ERROR$DETECTED;
600   8                   CALL TOP$DISPLAY (.REMOVE);
601   8                 END;
602   7                END;
603   6              END;
604   5            END;
605   4           END;
606   3         END;
607   2         MACHINE$STATE = BUSY;
608   2         CALL CLEAR$BOTTOM$DISPLAY;
609   2        END;

610   1     END;

MODULE INFORMATION:

CODE AREA SIZE    = 0793H   1939D
    VARIABLE AREA SIZE = 005FH    95D
    MAXIMUM STACK SIZE = 000AH    10D
    689 LINES READ
    0 PROGRAM ERRORS

END OF PL/M-80 COMPILATION

ISIS-II PL/M-80 V4.0 COMPILATION OF MODULE DATACOLLECTION
OBJECT MODULE PLACED IN :F1:DATAC.OBJ
COMPILER INVOKED BY:  PLM80 :F1:DATAC.PLM $ TITLE('MOTOMCO 919 AUTOMATIC DATA COLLECTION ROUTINES')
         $ DATE(28 MAY 83)
         $ DEBUG
                                         © 1983 DICKEY-john
Corporation--.
   1       DATA$COLLECTION: DO;

2   1     DECLARE FALSE LITERALLY '0';
   3   1     DECLARE TRUE LITERALLY '0FFH';

4   1     DECLARE COLLECTING$DATA BYTE EXTERNAL;
```

```
 5   1       DECLARE COUNTING BYTE EXTERNAL;
 6   1       DECLARE DATA$AVAILABLE BYTE EXTERNAL;
 7   1       DECLARE DATA$COLLECTION$COMPLETE BYTE EXTERNAL;
 8   1       DECLARE DATA$COLLECTION$ERROR BYTE EXTERNAL;
 9   1       DECLARE DATA$PENDING BYTE EXTERNAL;
10   1       DECLARE DUMP$CELL$DOWN BYTE EXTERNAL;
11   1       DECLARE ERROR BYTE EXTERNAL;
12   1       DECLARE MEASURING$TEMPERATURE BYTE EXTERNAL;
13   1       DECLARE RESET$PENDING BYTE EXTERNAL;
14   1       DECLARE SEEKING$MINIMUM BYTE EXTERNAL;
15   1       DECLARE SETTLING BYTE EXTERNAL;

16   1       DECLARE ABSOLUTE$MINIMUM BYTE EXTERNAL;
17   1       DECLARE AVERAGE BYTE EXTERNAL;
18   1       DECLARE DATA$POINT(8) BYTE EXTERNAL;
19   1       DECLARE EMPTY$CELL$DATA(6) ADDRESS EXTERNAL;
20   1       DECLARE FULL$CELL$DATA(2) ADDRESS EXTERNAL;
21   1       DECLARE HOME ADDRESS EXTERNAL;
22   1       DECLARE I ADDRESS EXTERNAL;
23   1       DECLARE INDEX BYTE EXTERNAL;
24   1       DECLARE J ADDRESS EXTERNAL;
25   1       DECLARE MINIMUM BYTE EXTERNAL;
26   1       DECLARE POINTER BYTE EXTERNAL;
27   1       DECLARE READING BYTE EXTERNAL;
28   1       DECLARE SAMPLE$NUMBER ADDRESS EXTERNAL;
29   1       DECLARE SETTLE$TIMER ADDRESS EXTERNAL;
30   1       DECLARE SUM ADDRESS EXTERNAL;
31   1       DECLARE TEMPERATURE$INDEX BYTE EXTERNAL;
32   1       DECLARE TEMPERATURE$TIMER ADDRESS EXTERNAL;

33   1       DECLARE P0 BYTE AT (.DATA$POINT(0));
34   1       DECLARE P1 BYTE AT (.DATA$POINT(1));
35   1       DECLARE P2 BYTE AT (.DATA$POINT(2));
36   1       DECLARE P3 BYTE AT (.DATA$POINT(3));
37   1       DECLARE P4 BYTE AT (.DATA$POINT(4));
38   1       DECLARE P5 BYTE AT (.DATA$POINT(5));
39   1       DECLARE P6 BYTE AT (.DATA$POINT(6));
40   1       DECLARE P7 BYTE AT (.DATA$POINT(7));

41   1       DECLARE NETWORK$TABLE(6) BYTE EXTERNAL;

42   1       DECLARE CHECKING(8) BYTE EXTERNAL;
43   1       DECLARE TESTING(8)  BYTE EXTERNAL;

44   1       DECLARE CODE$MESSAGE(16)        BYTE EXTERNAL;
45   1       DECLARE PLEASE$WAIT$MESSAGE(16) BYTE EXTERNAL;

46   1       BEEP: PROCEDURE (BEEP$TIME) EXTERNAL;
47   2          DECLARE BEEP$TIME ADDRESS;
48   2       END;

49   1       BOTTOM$DISPLAY: PROCEDURE (BOTTOM$POINTER) EXTERNAL;
50   2          DECLARE BOTTOM$POINTER ADDRESS;
51   2       END;
```

```
52   1      PULSE$DOOR$SOLENOID: PROCEDURE EXTERNAL;
53   2      END;

54   1      RESET$CELL$SHORT: PROCEDURE EXTERNAL;
55   2      END;

56   1      SELECT$NETWORK: PROCEDURE EXTERNAL;
57   2      END;

58   1      SET$CELL$SHORT: PROCEDURE EXTERNAL;
59   2      END;

60   1      STEP$MOTOR: PROCEDURE EXTERNAL;
61   2      END;

62   1      TIMER: PROCEDURE (TIME$COUNT) EXTERNAL;
63   2         DECLARE TIME$COUNT ADDRESS;
64   2      END;

65   1      TOP$DISPLAY: PROCEDURE (TOP$POINTER) EXTERNAL;
66   2         DECLARE TOP$POINTER ADDRESS;
67   2      END;
68   1      EMPTY$CELL: PROCEDURE PUBLIC;
69   2         DATA$AVAILABLE = FALSE;
70   2         DATA$COLLECTION$COMPLETE = FALSE;
71   2         DATA$COLLECTION$ERROR = FALSE;
72   2         DATA$PENDING = FALSE;
73   2         ERROR = FALSE;
74   2         INDEX = 0;
75   2         POINTER = 0;
76   2         SEEKING$MINIMUM = FALSE;
77   2         SETTLING = FALSE;
78   2         CALL SELECT$NETWORK;
79   2         CALL RESET$CELL$SHORT;
80   2         CALL TIMER (100);
81   2         DO I = 0 TO 5;
82   3            EMPTY$CELL$DATA(I) = 0;
83   3         END;
84   2         COLLECTING$DATA = TRUE;
85   2         DO I = 1 TO 4800;
86   3            DO WHILE NOT DATA$AVAILABLE;
87   4            END;
88   3            DATA$AVAILABLE = FALSE;
89   3            IF SETTLING THEN DO;
91   4               SETTLE$TIMER = SETTLE$TIMER - 1;
92   4               IF SETTLE$TIMER = 0 THEN DO;
94   5                  SETTLING = FALSE;
95   5               END;
96   4            END;
97   3            ELSE DO;
98   4               DATA$POINT(POINTER) = READING;
99   4               POINTER = (POINTER + 1 AND 7);
100  4               IF SEEKING$MINIMUM THEN DO;
102  5                  AVERAGE = SHR(P0+P1+P2+P3+P4+P5+P6+P7,8);
103  5                  IF AVERAGE < MINIMUM THEN DO;
105  6                     MINIMUM = AVERAGE;
106  6                     EMPTY$CELL$DATA(INDEX) = I;
```

```
107  6              END;
108  5           ELSE DO;
109  6              IF READING > ABSOLUTE$MINIMUM + 40 THEN DO;
111  7                 SEEKING$MINIMUM = FALSE;
112  7                 IF INDEX = 5 THEN DO;
114  8                    DATA$COLLECTION$COMPLETE = TRUE;
115  8                 END;
116  7                 ELSE DO;
117  8                    INDEX = INDEX + 1;
118  8                    CALL SELECT$NETWORK;
119  8                 END;
120  7                 SETTLING = TRUE;
121  7                 SETTLE$TIMER = 32;
122  7              END;
123  6           END;
124  5           END;
125  4        ELSE DO;
126  5           IF READING < ABSOLUTE$MINIMUM + 20 THEN DO;
128  6              IF DATA$COLLECTION$COMPLETE THEN DO;
130  7                 DATA$COLLECTION$ERROR = TRUE;
131  7              END;
132  6              ELSE DO;
133  7                 MINIMUM = READING;
134  7                 SEEKING$MINIMUM = TRUE;
135  7              END;
136  6           END;
137  5        END;
138  4     END;
139  3  END;
140  2  COLLECTING$DATA = FALSE;
141  2  CALL SET$CELL$SHORT;
142  2  DO INDEX = 0 TO 5;
143  3     EMPTY$CELL$DATA(INDEX) = EMPTY$CELL$DATA(INDEX) - 4;
144  3  END;
145  2  EMPTY$CELL$DATA(3) = 4801 - EMPTY$CELL$DATA(3);
146  2  EMPTY$CELL$DATA(4) = 4801 - EMPTY$CELL$DATA(4);
147  2  EMPTY$CELL$DATA(5) = 4801 - EMPTY$CELL$DATA(5);
148  2  IF NOT DATA$COLLECTION$COMPLETE THEN DO;
150  3     DATA$COLLECTION$ERROR = TRUE;
151  3  END;
152  2  IF DATA$COLLECTION$ERROR THEN DO;
154  3     IF NOT ERROR THEN DO;
156  4        ERROR = TRUE;
157  4        CALL BOTTOM$DISPLAY (.CODE$MESSAGE);
158  4     END;
159  3  END;
160  2  END;

161  1  FULL$CELL: PROCEDURE PUBLIC;
162  2     DATA$AVAILABLE = FALSE;
163  2     DATA$COLLECTION$COMPLETE = FALSE;
164  2     DATA$COLLECTION$ERROR = FALSE;
165  2     DATA$PENDING = FALSE;
166  2     ERROR = FALSE;
167  2     INDEX = 0;
168  2     POINTER = 0;
169  2     SEEKING$MINIMUM = FALSE;
170  2     SETTLING = FALSE;
171  2     CALL SELECT$NETWORK;
172  2     CALL RESET$CELL$SHORT;
173  2     CALL TIMER (100);
174  2     FULL$CELL$DATA(0) = 0;
```

```
175  2      FULL$CELL$DATA(1) = 1;
176  2      COLLECTING$DATA = TRUE;
177  2      DO I = 1 TO 4800;
178  3         DO WHILE NOT DATA$AVAILABLE;
179  4         END;
180  3         DATA$AVAILABLE = FALSE;
181  3         IF SETTLING THEN DO;
183  4            SETTLE$TIMER = SETTLE$TIMER - 1;
184  4            IF SETTLE$TIMER = 0 THEN DO;
186  5               SETTLING = FALSE;
187  5            END;
188  4         END;
189  3         ELSE DO;
190  4            DATA$POINT(POINTER) = READING;
191  4            POINTER = (POINTER + 1 AND 7);
192  4            IF SEEKING$MINIMUM THEN DO;
194  5               AVERAGE = SHR(P0+P1+P2+P3+P4+P5+P6+P7,8);
195  5               IF AVERAGE < MINIMUM THEN DO;
197  6                  MINIMUM = AVERAGE;
198  6                  FULL$CELL$DATA(INDEX) = I;
199  6               END;
200  5               ELSE DO;
201  6                  IF READING > ABSOLUTE$MINIMUM + 40 THEN DO;
203  7                     SEEKING$MINIMUM = FALSE;
204  7                     IF INDEX = 1 THEN DO;
206  8                        DATA$COLLECTION$COMPLETE = TRUE;
207  8                     END;
208  7                     ELSE DO;
209  8                        INDEX = INDEX + 1;
210  8                     END;
211  7                     SETTLING = TRUE;
212  7                     SETTLE$TIMER = 32;
213  7                  END;
214  6               END;
215  5            END;
216  4            ELSE DO;
217  5               IF READING < ABSOLUTE$MINIMUM + 20 THEN DO;
219  6                  IF DATA$COLLECTION$COMPLETE THEN DO;
221  7                     DATA$COLLECTION$ERROR = TRUE;
222  7                  END;
223  6                  ELSE DO;
224  7                     MINIMUM = READING;
225  7                     SEEKING$MINIMUM = TRUE;
226  7                  END;
227  6               END;
228  5            END;
229  4         END;
230  3      END;
231  2      COLLECTING$DATA = FALSE;
232  2      CALL SET$CELL$SHORT;
233  2      FULL$CELL$DATA(0) = FULL$CELL$DATA(0) - 4;
234  2      FULL$CELL$DATA(1) = FULL$CELL$DATA(1) - 4;
235  2      FULL$CELL$DATA(1) = 4801 - FULL$CELL$DATA(1);
236  2      IF NOT DATA$COLLECTION$COMPLETE THEN DO;
238  3         DATA$COLLECTION$ERROR = TRUE;
239  3      END;
240  2      IF DATA$COLLECTION$ERROR THEN DO;
242  3         IF NOT ERROR THEN DO;
244  4            ERROR = TRUE;
245  4            CALL BOTTOM$DISPLAY (.CODE$MESSAGE);
246  4         END;
247  3      END;
248  2   END;
```

```
249  1    GO$HOME: PROCEDURE PUBLIC;
250  2      CALL TOP$DISPLAY (.CHECKING);
251  2      CALL BOTTOM$DISPLAY (.PLEASE$WAIT$MESSAGE);
252  2      DATA$AVAILABLE = FALSE;
253  2      DATA$PENDING = FALSE;
254  2      ERROR = FALSE;
255  2      INDEX = 0;
256  2      RESET$PENDING = TRUE;
257  2      CALL SELECT$NETWORK;
258  2      CALL RESET$CELL$SHORT;
259  2      CALL TIMER(100);
260  2      COLLECTING$DATA = TRUE;
261  2      DO WHILE NOT DATA$AVAILABLE;
262  3      END;
263  2      DATA$AVAILABLE = FALSE;
264  2      DO WHILE (READING < 80H) AND DUMP$CELL$DOWN;
265  3        DO WHILE NOT DATA$AVAILABLE;
266  4        END;
267  3        DATA$AVAILABLE = FALSE;
268  3      END;
269  2      COLLECTING$DATA = FALSE;
270  2      IF NOT ERROR THEN DO;
272  3        ABSOLUTE$MINIMUM = 0FFH;
273  3        COLLECTING$DATA = TRUE;
274  3        DO I = 1 TO 4800;
275  4          DO WHILE NOT DATA$AVAILABLE;
276  5          END;
277  4          DATA$AVAILABLE = FALSE;
278  4          IF READING < ABSOLUTE$MINIMUM THEN DO;
280  5            ABSOLUTE$MINIMUM = READING;
281  5          END;
282  4        END;
283  3        COLLECTING$DATA = FALSE;
284  3        IF NOT ERROR THEN DO;
286  4          CALL FULL$CELL;
287  4          IF NOT ERROR THEN DO;
289  5            FULL$CELL$DATA(1) = 4801 - FULL$CELL$DATA(1);
290  5            IF (FULL$CELL$DATA(1) - FULL$CELL$DATA(0)) < 2400 THEN DO;
292  6              HOME = (FULL$CELL$DATA(0) + FULL$CELL$DATA(1)) / 2;
293  6            END;
294  5            ELSE DO ;
295  6              HOME = (FULL$CELL$DATA(0) + FULL$CELL$DATA(1) + 4800) / 2;
296  6              IF HOME >= 4800 THEN DO;
298  7                HOME = HOME - 4800;
299  7              END;
300  6            END;
301  5            IF HOME > 0 THEN DO;
303  6              DO I = 1 TO HOME;
304  7                CALL STEP$MOTOR;
305  7                HALT;
306  7                HALT;
307  7              END;
308  6            END;
309  5            FULL$CELL$DATA(1) = 4801 - FULL$CELL$DATA(1);
310  5          END;
311  4        END;
312  3      END;
313  2      CALL SET$CELL$SHORT;
314  2    END;

315  1    DATA$COLLECTION: PROCEDURE PUBLIC;
316  2      RESET$PENDING = TRUE;
```

```
317  2        CALL TOP$DISPLAY (.TESTING);
318  2        TEMPERATURE$INDEX = 0;
319  2        TEMPERATURE$TIMER = 1;
320  2        COUNTING = FALSE;
321  2        MEASURING$TEMPERATURE = TRUE;
322  2        CALL EMPTY$CELL;
323  2        IF NOT ERROR THEN DO;
325  3          DO WHILE MEASURING$TEMPERATURE;
326  4          END;
327  3          CALL PULSE$DOOR$SOLENOID;
328  3          IF NOT ERROR THEN DO;
330  4            CALL TIMER (500);
331  4            CALL FULL$CELL;
332  4            IF NOT ERROR THEN DO;
334  5              SAMPLE$NUMBER = SAMPLE$NUMBER + 1;
335  5            END;
336  4          END;
337  3        END;
338  2     END;

339  1     END;

MODULE INFORMATION:

CODE AREA SIZE     = 054BH    1355D
    VARIABLE AREA SIZE = 0000H      0D
    MAXIMUM STACK SIZE = 0004H      4D
    358 LINES READ
    0 PROGRAM ERRORS

END OF PL/M-80 COMPILATION

ISIS-II PL/M-80 V4.0 COMPILATION OF MODULE SUBROUTINES
OBJECT MODULE PLACED IN :F1:PLMSUB.OBJ
COMPILER INVOKED BY:  PLM80 :F1:PLMSUB.PLM $ TITLE('MOTOMCO 919 AUTOMATIC SUBROUTINES')
          $ DATE(27 MAY 83)
          $ DEBUG (c) 1983 DICKEY-john
Corporation--.
  1        SUBROUTINES: DO;

2  1     DECLARE CARRIAGE$RETURN LITERALLY '0DH';
  3  1     DECLARE DECIMAL$POINT LITERALLY '2EH';
  4  1     DECLARE FALSE LITERALLY '0';
  5  1     DECLARE LINE$FEED LITERALLY '0AH';
  6  1     DECLARE MINUS$SIGN LITERALLY '2DH';
  7  1     DECLARE NEGATIVE LITERALLY '80H';
  8  1     DECLARE POSITIVE LITERALLY '0';
  9  1     DECLARE SPACE LITERALLY '20H';
 10  1     DECLARE TRUE LITERALLY '0FFH';
 11  1     DECLARE ZERO LITERALLY '30H';
```

```
12   1         DECLARE ERROR BYTE EXTERNAL;
13   1         DECLARE FAHRENHEIT BYTE EXTERNAL;

14   1         DECLARE BEEP$TIMER ADDRESS EXTERNAL;
15   1         DECLARE BUFFER(6) BYTE EXTERNAL;
16   1         DECLARE INDEX BYTE EXTERNAL;
17   1         DECLARE J ADDRESS EXTERNAL;
18   1         DECLARE MOTOR$STEP BYTE EXTERNAL;
19   1         DECLARE PORT$1$DATA BYTE EXTERNAL;
20   1         DECLARE PORT$3$DATA BYTE EXTERNAL;
21   1         DECLARE REGISTER$1(5) BYTE EXTERNAL;
22   1         DECLARE REGISTER$2(5) BYTE EXTERNAL;
23   1         DECLARE SAMPLE$NUMBER ADDRESS EXTERNAL;

24   1         DECLARE A$EMPTY$CELL      ADDRESS EXTERNAL;
25   1         DECLARE B$EMPTY$CELL      ADDRESS EXTERNAL;
26   1         DECLARE A$TEST$NETWORK$1 ADDRESS EXTERNAL;
27   1         DECLARE B$TEST$NETWORK$1 ADDRESS EXTERNAL;
28   1         DECLARE A$TEST$NETWORK$2 ADDRESS EXTERNAL;
29   1         DECLARE B$TEST$NETWORK$2 ADDRESS EXTERNAL;

30   1         DECLARE A$FULL$CELL ADDRESS EXTERNAL;
31   1         DECLARE B$FULL$CELL ADDRESS EXTERNAL;

32   1         DECLARE SIGNX BYTE EXTERNAL;
33   1         DECLARE EXPX BYTE EXTERNAL;
34   1         DECLARE LSBX BYTE EXTERNAL;
35   1         DECLARE X(4) BYTE AT (.LSBX);

36   1         DECLARE NETWORK$TABLE(6) BYTE EXTERNAL;
37   1         DECLARE STEP$SEQUENCE(8) BYTE EXTERNAL;

38   1         DECLARE CODE$MESSAGE(16) BYTE EXTERNAL;

39   1         DECLARE CONSTANT$N500000EP000(5) BYTE EXTERNAL;
40   1         DECLARE CONSTANT$P500000EP000(5) BYTE EXTERNAL;
41   1         DECLARE CONSTANT$P200000EP001(5) BYTE EXTERNAL;
42   1         DECLARE CONSTANT$P500000EP001(5) BYTE EXTERNAL;

43   1         BCDADD: PROCEDURE EXTERNAL;
44   2         END;

45   1         BCDDIV: PROCEDURE EXTERNAL;
46   2         END;

47   1         BCDMUL: PROCEDURE EXTERNAL;
48   2         END;

49   1         BCDSUB: PROCEDURE EXTERNAL;
50   2         END;
```

```
51  1    FIX: PROCEDURE (POSITION) EXTERNAL;
52  2       DECLARE POSITION BYTE;
53  2    END;

54  1    LOAD: PROCEDURE (POINTER) EXTERNAL;
55  2       DECLARE POINTER ADDRESS;
56  2    END;

57  1    OC: PROCEDURE (CHARACTER) EXTERNAL;
58  2       DECLARE CHARACTER BYTE;
59  2    END;

60  1    STORE: PROCEDURE (POINTER) EXTERNAL;
61  2       DECLARE POINTER ADDRESS;
62  2    END;

63  1    BEEPER$ON: PROCEDURE BYTE PUBLIC;
64  2       IF (PORT$3$DATA AND 2) = 2 THEN RETURN TRUE;
66  2       ELSE RETURN FALSE;
67  2    END;

68  1    CELL$DOWN: PROCEDURE BYTE PUBLIC;
69  2       IF (INPUT(2) AND 1) = 0 THEN RETURN TRUE;
71  2       ELSE RETURN FALSE;
72  2    END;

73  1    CELL$UP: PROCEDURE BYTE PUBLIC;
74  2       IF (INPUT(2) AND 2) = 0 THEN RETURN TRUE;
76  2       ELSE RETURN FALSE;
77  2    END;

78  1    DATA$TERMINAL$READY: PROCEDURE BYTE PUBLIC;
79  2       IF (INPUT(2) AND 10H) = 0 THEN RETURN TRUE;
81  2       ELSE RETURN FALSE;
82  2    END;

83  1    KEY$DATA: PROCEDURE BYTE PUBLIC;
84  2       RETURN (NOT INPUT(18H));
85  2    END;

86  1    BEEP: PROCEDURE (BEEP$TIME) PUBLIC;
87  2       DECLARE BEEP$TIME ADDRESS;

88  2       BEEP$TIMER = BEEP$TIME;
89  2       PORT$3$DATA = (PORT$3$DATA OR 2);
90  2       OUTPUT(3) = PORT$3$DATA;
91  2    END;

92  1    OUTPUT$DISPLAY$CONTROL: PROCEDURE (CHARACTER) PUBLIC;
93  2       DECLARE CHARACTER BYTE;
```

```
94   2        DO WHILE (INPUT(10H) AND 80H) = 80H;
95   3        END;
96   2        OUTPUT(10H) = CHARACTER;
97   2     END;

98   1     OUTPUT$DISPLAY$DATA: PROCEDURE (CHARACTER);
99   2        DECLARE CHARACTER BYTE;

100  2        DO WHILE (INPUT(10H) AND 80H) = 80H;
101  3        END;
102  2        OUTPUT(11H) = CHARACTER;
103  2     END;
104  1     RESET$CELL$SHORT: PROCEDURE PUBLIC;
105  2        PORT$1$DATA = (PORT$1$DATA OR 40H);
106  2        OUTPUT(1) = PORT$1$DATA;
107  2     END;

108  1     SELECT$NETWORK: PROCEDURE PUBLIC;
109  2        PORT$1$DATA = ((PORT$1$DATA AND 0CFH) OR NETWORK$TABLE(INDEX));
110  2        OUTPUT(1) = PORT$1$DATA;
111  2     END;

112  1     SET$CELL$SHORT: PROCEDURE PUBLIC;
113  2        PORT$1$DATA = (PORT$1$DATA AND 0BFH);
114  2        OUTPUT(1) = PORT$1$DATA;
115  2     END;

116  1     SOLENOID$OFF: PROCEDURE;
117  2        PORT$1$DATA = (PORT$1$DATA AND 7FH);
118  2        OUTPUT(1) = PORT$1$DATA;
119  2     END;

120  1     SOLENOID$ON: PROCEDURE;
121  2        PORT$1$DATA = (PORT$1$DATA OR 80H);
122  2        OUTPUT(1) = PORT$1$DATA;
123  2     END;

124  1     STEP$MOTOR: PROCEDURE PUBLIC;
125  2        MOTOR$STEP = (MOTOR$STEP + 1 AND 7);
126  2        PORT$1$DATA = ((PORT$1$DATA AND 0F0H) OR STEP$SEQUENCE(MOTOR$STEP));
127  2        OUTPUT(1) = PORT$1$DATA;
128  2     END;

129  1     BOTTOM$DISPLAY: PROCEDURE (POINTER) PUBLIC;
130  2        DECLARE POINTER ADDRESS;
131  2        DECLARE CHARACTER BASED POINTER BYTE;

132  2        CALL OUTPUT$DISPLAY$CONTROL (80H);
133  2        DO J = 1 TO 16;
134  3           CALL OUTPUT$DISPLAY$DATA (CHARACTER);
135  3           POINTER = POINTER + 1;
136  3        END;
137  2     END;
```

```
138  1    CLEAR$BOTTOM$DISPLAY: PROCEDURE PUBLIC;
139  2        CALL OUTPUT$DISPLAY$CONTROL (80H);
140  2        DO J = 1 TO 16;
141  3           CALL OUTPUT$DISPLAY$DATA (SPACE);
142  3        END;
143  2    END;
144  1    CLEAR$TOP$DISPLAY: PROCEDURE PUBLIC;
145  2        CALL OUTPUT$DISPLAY$CONTROL (90H);
146  2        DO J = 1 TO 8;
147  3           CALL OUTPUT$DISPLAY$DATA (SPACE);
148  3        END;
149  2    END;

150  1    TIMER: PROCEDURE (TIME$COUNT) PUBLIC;
151  2        DECLARE TIME$COUNT ADDRESS;

152  2        DO J = 1 TO TIME$COUNT;
153  3           HALT;
154  3        END;
155  2    END;

156  1    TOP$DISPLAY: PROCEDURE (POINTER) PUBLIC;
157  2        DECLARE POINTER ADDRESS;
158  2        DECLARE CHARACTER BASED POINTER BYTE;

159  2        CALL OUTPUT$DISPLAY$CONTROL (90H);
160  2        DO J = 1 TO 8;
161  3           CALL OUTPUT$DISPLAY$DATA (CHARACTER);
162  3           POINTER = POINTER + 1;
163  3        END;
164  2    END;

165  1    UPPER: PROCEDURE (DIGITS) BYTE;
166  2        DECLARE DIGITS BYTE;

167  2        RETURN SHR(DIGITS,4);
168  2    END;

169  1    LOWER: PROCEDURE (DIGITS) BYTE;
170  2        DECLARE DIGITS BYTE;

171  2        RETURN DIGITS AND 0FH;
172  2    END;

173  1    LOAD$BUFFER: PROCEDURE;
174  2        BUFFER(0) = SPACE;
175  2        BUFFER(1) = SPACE;
176  2        IF (X(2) OR X(3)) = 0 THEN DO;
178  3           BUFFER(2) = SPACE;
179  3           BUFFER(3) = SPACE;
180  3           BUFFER(4) = SPACE;
181  3           BUFFER(5) = ZERO;
182  3        END;
183  2        ELSE DO;
```

```
184  3        BUFFER(2) = (UPPER(X(3)) OR 30H);
185  3        BUFFER(3) = (LOWER(X(3)) OR 30H);
186  3        BUFFER(4) = (UPPER(X(2)) OR 30H);
187  3        BUFFER(5) = (LOWER(X(2)) OR 30H);
188  3        DO CASE EXPX;
189  4           DO;
190  5              IF SIGNX = NEGATIVE THEN DO;
192  6                 BUFFER(0) = MINUS$SIGN;
193  6              END;
194  5           END;
195  4           DO;
196  5              BUFFER(1) = BUFFER(2);
197  5              BUFFER(2) = DECIMAL$POINT;
198  5              IF SIGNX = NEGATIVE THEN DO;
200  6                 BUFFER(0) = MINUS$SIGN;
201  6              END;
202  5           END;
203  4           DO;
204  5              BUFFER(1) = BUFFER(2);
205  5              BUFFER(2) = BUFFER(3);
206  5              BUFFER(3) = DECIMAL$POINT;
207  5              IF BUFFER(1) = ZERO THEN DO;
209  6                 BUFFER(1) = SPACE;
210  6              END;
211  5              IF SIGNX = NEGATIVE THEN DO;
213  6                 IF BUFFER(1) = SPACE THEN DO;
215  7                    BUFFER(1) = MINUS$SIGN;
216  7                 END;
217  6                 ELSE DO;
218  7                    BUFFER(0) = MINUS$SIGN;
219  7                 END;
220  6              END;
221  5           END;
222  4           DO;
223  5              BUFFER(1) = BUFFER(2);
224  5              BUFFER(2) = BUFFER(3);
225  5              BUFFER(3) = BUFFER(4);
226  5              BUFFER(4) = DECIMAL$POINT;
227  5              IF BUFFER(1) = ZERO THEN DO;
229  6                 BUFFER(1) = SPACE;
230  6                 IF BUFFER(2) = ZERO THEN DO;
232  7                    BUFFER(2) = SPACE;
233  7                 END;
234  6              END;
235  5              IF SIGNX = NEGATIVE THEN DO;
237  6                 IF BUFFER(2) = SPACE THEN DO;
239  7                    BUFFER(2) = MINUS$SIGN;
240  7                 END;
241  6                 ELSE DO;
242  7                    IF BUFFER(1) = SPACE THEN DO;
244  8                       BUFFER(1) = MINUS$SIGN;
245  8                    END;
246  7                    ELSE DO;
247  8                       BUFFER(0) = MINUS$SIGN;
248  8                    END;
249  7                 END;
250  6              END;
251  5           END;
252  4           DO;
253  5              IF BUFFER(2) = ZERO THEN DO;
255  6                 BUFFER(2) = SPACE;
256  6                 IF BUFFER(3) = ZERO THEN DO;
258  7                    BUFFER(3) = SPACE;
```

```
259  7              IF BUFFER(4) = ZERO THEN DO;
261  8                 BUFFER(4) = SPACE;
262  8              END;
263  7           END;
264  6         END;
265  5         IF SIGNX = NEGATIVE THEN DO;
267  6           IF BUFFER(4) = SPACE THEN DO;
269  7              BUFFER(4) = MINUS$SIGN;
270  7           END;
271  6           ELSE DO;
272  7              IF BUFFER(3) = SPACE THEN DO;
274  8                 BUFFER(3) = MINUS$SIGN;
275  8              END;
276  7              ELSE DO;
277  8                 IF BUFFER(2) = SPACE THEN DO;
279  9                    BUFFER(2) = MINUS$SIGN;
280  9                 END;
281  8                 ELSE DO;
282  9                    BUFFER(1) = MINUS$SIGN;
283  9                 END;
284  8              END;
285  7           END;
286  6         END;
287  5      END;
288  4    END;
289  3  END;
290  2  END;

291  1  DISPLAY$X: PROCEDURE PUBLIC;
292  2     CALL LOAD$BUFFER;
293  2     CALL OUTPUT$DISPLAY$CONTROL (90H);
294  2     DO INDEX = 0 TO 5;
295  3        CALL OUTPUT$DISPLAY$DATA (BUFFER(INDEX));
296  3     END;
297  2  END;

298  1  OUTPUT$X: PROCEDURE;
299  2     CALL LOAD$BUFFER;
300  2     DO INDEX = 0 TO 5;
301  3        CALL OC (BUFFER(INDEX));
302  3     END;
303  2     CALL OC (SPACE);
304  2     CALL OC (SPACE);
305  2  END;

306  1  LOAD$BINARY: PROCEDURE (BINARY$DATA);
307  2     DECLARE BINARY$DATA ADDRESS;

308  2     SIGNX = 0;
309  2     EXPX = 4;
310  2     X(3) = SHL(BINARY$DATA / 1000,4);
311  2     BINARY$DATA = BINARY$DATA MOD 1000;
312  2     X(3) = (X(3) OR (BINARY$DATA / 100));
313  2     BINARY$DATA = BINARY$DATA MOD 100;
314  2     X(2)= SHL(BINARY$DATA / 10,4);
315  2     BINARY$DATA = BINARY$DATA MOD 10;
316  2     X(2) = (X(2)OR (BINARY$DATA));
317  2     X(1) = 0;
```

```
318  2        X(0) = 0;
319  2        END;

320  1     LINEARIZE: PROCEDURE (BINARY$DATA);
321  2        DECLARE BINARY$DATA ADDRESS;

322  2        CALL LOAD$BINARY (BINARY$DATA);
323  2        END;

324  1     CALCULATE$AVERAGE$DIFFERENCE: PROCEDURE (A$BINARY$DATA,B$BINARY$DATA);
325  2        DECLARE A$BINARY$DATA ADDRESS;
326  2        DECLARE B$BINARY$DATA ADDRESS;

327  2        CALL LINEARIZE (B$EMPTY$CELL);
328  2        CALL STORE (.REGISTER$1);
329  2        CALL LINEARIZE (B$BINARY$DATA);
330  2        CALL LOAD (.REGISTER$1);
331  2        CALL BCDSUB;
332  2        CALL STORE (.REGISTER$1);
333  2        CALL LINEARIZE (A$EMPTY$CELL);
334  2        CALL STORE (.REGISTER$2);
335  2        CALL LINEARIZE (A$BINARY$DATA);
336  2        CALL LOAD (.REGISTER$2);
337  2        CALL BCDSUB;
338  2        CALL STORE (.REGISTER$2);
339  2        CALL LOAD (.REGISTER$1);
340  2        CALL BCDSUB;
341  2        SIGNX = POSITIVE;
342  2        CALL LOAD (.CONSTANT$P500000EP001);
343  2        CALL BCDSUB;
344  2        IF SIGNX = POSITIVE THEN DO;
346  3           ERROR = TRUE;
347  3           CALL BOTTOM$DISPLAY (.CODE$MESSAGE);
348  3        END;
349  2        CALL LOAD (.REGISTER$2);
350  2        CALL LOAD (.REGISTER$1);
351  2        CALL BCDADD;
352  2        CALL LOAD (.CONSTANT$P200000EP001);
353  2        CALL BCDDIV;
354  2        IF SIGNX = POSITIVE THEN DO;
356  3           CALL LOAD (.CONSTANT$P500000EP000);
357  3        END;
358  2        ELSE DO;
359  3           CALL LOAD (.CONSTANT$N500000EP000);
360  3        END;
361  2        CALL BCDADD;
362  2        CALL FIX (4);
363  2        END;

364  1     CALCULATE$CHART$DATA: PROCEDURE PUBLIC;
365  2        CALL CALCULATE$AVERAGE$DIFFERENCE (A$FULL$CELL,B$FULL$CELL);
366  2        END;

367  1     CALCULATE$TEST$NETWORK$1$DATA: PROCEDURE PUBLIC;
368  2        CALL CALCULATE$AVERAGE$DIFFERENCE (A$TEST$NETWORK$1,B$TEST$NETWORK$1);
369  2        END;
```

```
370  1    CALCULATE$TEST$NETWORK$2$DATA: PROCEDURE PUBLIC;
371  2       CALL CALCULATE$AVERAGE$DIFFERENCE (A$TEST$NETWORK$2,B$TEST$NETWORK$2);
372  2    END;

373  1    DISPLAY$GRAIN$NAME: PROCEDURE PUBLIC;
374  2       ;
375  2    END;

376  1    DISPLAY$SAMPLE$WEIGHT: PROCEDURE PUBLIC;
377  2       ;
378  2    END;

379  1    OUTPUT$CHART$DATA: PROCEDURE PUBLIC;
380  2       CALL LOAD$BINARY (SAMPLE$NUMBER);
381  2       CALL OUTPUT$X;
382  2       CALL CALCULATE$CHART$DATA;
383  2       CALL OUTPUT$X;
384  2       CALL OC (CARRIAGE$RETURN);
385  2       CALL OC (LINE$FEED);
386  2       CALL OC (LINE$FEED);
387  2    END;

388  1    OUTPUT$EMPTY$CELL$DATA: PROCEDURE PUBLIC;
389  2       CALL LOAD$BINARY (A$EMPTY$CELL);
390  2       CALL OUTPUT$X;
391  2       CALL LOAD$BINARY (B$EMPTY$CELL);
392  2       CALL OUTPUT$X;
393  2       CALL LOAD$BINARY (A$TEST$NETWORK$1);
394  2       CALL OUTPUT$X;
395  2       CALL LOAD$BINARY (B$TEST$NETWORK$1);
396  2       CALL OUTPUT$X;
397  2       CALL LOAD$BINARY (A$TEST$NETWORK$2);
398  2       CALL OUTPUT$X;
399  2       CALL LOAD$BINARY (B$TEST$NETWORK$2);
400  2       CALL OUTPUT$X;
401  2       CALL OC (CARRIAGE$RETURN);
402  2       CALL OC (LINE$FEED);
403  2       CALL OC (LINE$FEED);
404  2       CALL TIMER (100);
405  2       CALL LINEARIZE (A$EMPTY$CELL);
406  2       CALL OUTPUT$X;
407  2       CALL LINEARIZE (B$EMPTY$CELL);
408  2       CALL OUTPUT$X;
409  2       CALL LINEARIZE (A$TEST$NETWORK$1);
410  2       CALL OUTPUT$X;
411  2       CALL LINEARIZE (B$TEST$NETWORK$1);
412  2       CALL OUTPUT$X;
413  2       CALL LINEARIZE (A$TEST$NETWORK$2);
414  2       CALL OUTPUT$X;
415  2       CALL LINEARIZE (B$TEST$NETWORK$2);
416  2       CALL OUTPUT$X;
417  2       CALL CALCULATE$TEST$NETWORK$1$DATA;
418  2       CALL OUTPUT$X;
419  2       CALL CALCULATE$TEST$NETWORK$2$DATA;
420  2       CALL OUTPUT$X;
421  2       CALL OC (CARRIAGE$RETURN);
422  2       CALL OC (LINE$FEED);
423  2       CALL OC (LINE$FEED);
424  2    END;
```

```
425  1      OUTPUT$FULL$CELL$DATA: PROCEDURE PUBLIC;
426  2        CALL LOAD$BINARY (A$FULL$CELL);
427  2        CALL OUTPUT$X;
428  2        CALL LOAD$BINARY (B$FULL$CELL);
429  2        CALL OUTPUT$X;
430  2        CALL LINEARIZE (A$FULL$CELL);
431  2        CALL OUTPUT$X;
432  2        CALL LINEARIZE (B$FULL$CELL);
433  2        CALL OUTPUT$X;
434  2        CALL CALCULATE$CHART$DATA;
435  2        CALL OUTPUT$X;
436  2        CALL OC (CARRIAGE$RETURN);
437  2        CALL OC (LINE$FEED);
438  2        CALL OC (LINE$FEED);
439  2      END;

440  1      OUTPUT$TEMPERATURE$DATA: PROCEDURE PUBLIC;
441  2        ;
442  2      END;

443  1      PULSE$DOOR$SOLENOID: PROCEDURE PUBLIC;
444  2        IF (INPUT(2) AND 4) = 1 THEN DO;
446  3          ERROR = TRUE;
447  3          CALL BOTTOM$DISPLAY (.CODE$MESSAGE);
448  3        END;
449  2        ELSE DO;
450  3          CALL SOLENOID$ON;
451  3          CALL TIMER (500);
452  3          IF (INPUT(2) AND 4) = 0 THEN DO;
454  4            ERROR = TRUE;
455  4            CALL BOTTOM$DISPLAY (.CODE$MESSAGE);
456  4          END;
457  3          CALL SOLENOID$OFF;
458  3          CALL TIMER (100);
459  3          IF (INPUT(2) AND 4) = 1 THEN DO;
461  4            ERROR = TRUE;
462  4            CALL BOTTOM$DISPLAY (.CODE$MESSAGE);
463  4          END;
464  3        END;
465  2      END;

466  1      END;
```

MODULE INFORMATION:

```
    CODE AREA SIZE     = 06B8H    1720D
    VARIABLE AREA SIZE = 0014H      20D
    MAXIMUM STACK SIZE = 000CH      12D
    581 LINES READ
    0 PROGRAM ERRORS
```

END OF PL/M-80 COMPILATION

```
ISIS-II 8080/8085 MACRO ASSEMBLER, V4.1      MATH
BCD MATH PACKAGE   3 JUN 83  D.E.GRIM

LOC  OBJ       LINE    SOURCE STATEMENT
                                    © 1983 DICKEY-john Corporation--.
                1 $    TITLE('BCD MATH PACKAGE   3 JUN 83  D.E.GRIM')
                2 $    MOD85
                3 $    DEBUG
                4 ;
                5 ;
                6 ;    THE ROUTINES THAT COMPRISE THIS MODULE CONSTITUTE A PL/M-80
                7 ;    COMPATIBLE BCD MATH PACKAGE.  THE PACKAGE PROVIDES FOR THE
                8 ;    ADDITION, SUBTRACTION, MULTIPLICATION AND DIVISION OF SIX DIGIT
                9 ;    FLOATING POINT NUMBERS.
               10 ;
               11 ;    MATHMATICAL OPERATIONS ARE EXECUTED USING THE REVERSE POLISH
               12 ;    NOTATION (RPN) METHOD.  THE OPERATIONAL STACK CONSISTS OF FOUR
               13 ;    SIX BYTE WORKING VARIABLES ARRANGED AS SHOWN BELOW.
               14 ;
               15 ;            SIGN T              MOST SIGNIFICANT BYTE OF STACK
               16 ;            EXPONENT T
               17 ;            T7,T6
               18 ;            T5,T4
               19 ;            T3,T2
               20 ;            T1,T0
               21 ;
               22 ;            SIGN Z
               23 ;            EXPONENT Z
               24 ;            Z7,Z6
               25 ;            Z5,Z4
               26 ;            Z3,Z2
               27 ;            Z1,Z0
               28 ;
               29 ;            SIGN Y
               30 ;            EXPONENT Y
               31 ;            Y7,Y6
               32 ;            Y5,Y4
               33 ;            Y3,Y2
               34 ;            Y1,Y0
               35 ;
               36 ;            SIGN X
               37 ;            EXPONENT X;
               38 ;            X7,X6
               39 ;            X5,X4
               40 ;            X3,X2
               41 ;            X1,X0               LEAST SIGNIFICANT BYTE OF STACK
               42 ;
               43 ;    NOTE THAT THE STACK VARIABLES ARE EIGHT DIGITS IN LENGTH.  THE
               44 ;    TWO EXTRA DIGITS ARE REQUIRED FOR COMPUTATIONAL PURPOSES ONLY.
               45 ;    ALL RESULTS ARE ROUNDED TO 6 DIGITS;
               46 ;
               47 ;    STACK VARIABLES ARE OF THE FORM:
               48 ;            SIGN .76543210 * 10^EXPONENT
               49 ;
               50 ;    WHERE:  A POSITIVE NUMBER IS DENOTED BY SIGN = 0 AND
               51 ;            A NEGATIVE NUMBER IS DENOTED BY SIGN = 80H AND
               52 ;            -128 <= EXPONENT <= 127
               53 ;
               54 ;    NUMBERS ROUNDED TO SIX DIGITS ARE OF THE FORM:
               55 ;            SIGN .76543200 * 10^EXPONENT
               56 ;
```

| LOC  OBJ | LINE | SOURCE STATEMENT |
|---|---|---|
| | 57 ; | IF DIVISION BY 0 IS ATTEMPTED A FLAG NAMED 'DIVO' IS SET |
| | 58 ; | TO FFH AND NO OPERATION IS PERFORMED |
| | 59 ; | |
| | 60 ; | THE FOLLOWING PL/M-80 COMPATIBLE ROUTINES MAY BE CALLED BY THE USER: |
| | 61 ; | |
| | 62 ; | BCDADD   X = Y + X, Y <- Z, Z <- T |
| | 63 ; | BCDSUB   X = Y - X, Y <- Z, Z <- T |
| | 64 ; | BCDMUL   X = Y * X, Y <- Z, Z <- T |
| | 65 ; | BCDDIV   X = Y / X, Y <- Z, Z <- T |
| | 66 ; | LOAD     Z -> T, Y -> Z, X -> Y, SIX DIGIT VARIABLE -> X |
| | 67 ; | STORE    SIX DIGIT VARIABLE <- X |
| | 68 ; | FIX      FIX DECIMAL POINT |
| | 69 ; | |
| | 70 ;******************************************************************** | |
| | 71 ; | |
| | 72 | NAME   MATH |
| | 73 ; | |
| | 74 | PUBLIC  BCDADD,BCDSUB,BCDMUL,BCDDIV |
| | 75 | PUBLIC  LOAD,STORE,FIX,CLEARX,CHGSNX |
| | 76 | PUBLIC  X,EXPX,SIGNX,DIVO |
| | 77 ; | |
| | 78 | DSEG |
| | 79 ; | |
| 0000 | 80 X:     | DS   4 |
| 0004 | 81 EXPX:  | DS   1 |
| 0005 | 82 SIGNX: | DS   1 |
| 0006 | 83 Y:     | DS   4 |
| 000A | 84 EXPY:  | DS   1 |
| 000B | 85 SIGNY: | DS   1 |
| 000C | 86 Z:     | DS   4 |
| 0010 | 87 EXPZ:  | DS   1 |
| 0011 | 88 SIGNZ: | DS   1 |
| 0012 | 89 T:     | DS   4 |
| 0016 | 90 EXPT:  | DS   1 |
| 0017 | 91 SIGNT: | DS   1 |
| 0018 | 92 S:     | DS   4 |
| 001C | 93 DIVO:  | DS   1; |
| | 94 ; | |
| | 95 | CSEG |
| | 96 ; | |
| | 97 ;******************************************************************** | |
| | 98 ; | |
| | 99 ; | ADDITION ROUTINE |
| | 100 ; | |
| | 101 ; | NORMALIZE X |
| | 102 ; | NORMALIZE Y |
| | 103 ; | IF MANTISSA X = 0 THEN |
| | 104 ; |    X <- Y |
| | 105 ; | ELSE |
| | 106 ; |    IF MANTISSA Y <> 0 THEN |
| | 107 ; |       DO WHILE EXPONENT X <> EXPONENT Y |
| | 108 ; |          IF EXPONENT X < EXPONENT Y THEN |
| | 109 ; |             SHIFT MANTISSA X RIGHT ONE DIGIT |
| | 110 ; |             INCREMENT EXPONENT X |
| | 111 ; |          ELSE |
| | 112 ; |             SHIFT MANTISSA Y RIGHT ONE DIGIT |
| | 113 ; |             INCREMENT EXPONENT Y |
| | 114 ; |          END |
| | 115 ; |       END |
| | 116 ; | SHIFT MANTISSA X RIGHT ONE DIGIT |
| | 117 ; | INCREMENT EXPONENT X |

| LOC OBJ | LINE | SOURCE STATEMENT |
|---|---|---|
| | 118 ; | SHIFT MANTISSA Y RIGHT ONE DIGIT |
| | 119 ; | INCREMENT EXPONENT Y |
| | 120 ; | IF SIGN X = SIGN Y THEN |
| | 121 ; |   MANTISSA X = MANTISSA Y + MANTISSA X |
| | 122 ; | ELSE |
| | 123 ; |   IF MANTISSA X <= MANTISSA Y THEN |
| | 124 ; |     MANTISSA X = MANTISSA Y - MANTISSA X |
| | 125 ; |     CHANGE SIGN X |
| | 126 ; |   ELSE |
| | 127 ; |     MANTISSA X = MANTISSA X - MANTISSA Y |
| | 128 ; |   END |
| | 129 ; | END |
| | 130 ; | IF MANTISSA X = 0 THEN |
| | 131 ; |   SIGN X = POSITIVE |
| | 132 ; |   EXPONENT X = 0 |
| | 133 ; | ELSE DO |
| | 134 ; |   NORMALIZE X |
| | 135 ; |   ROUND X TO SIX DIGITS |
| | 136 ; | END |
| | 137 ; | END |
| | 138 ; | END |
| | 139 ; | Y <- Z |
| | 140 ; | Z <- T |
| | 141 ; | |
| | 142 ; | |
| | 143 ; | NORMALIZE X |
| | 144 ; | |
| 0000 CDB802 C | 145 BCDADD: | CALL NORMX |
| | 146 ; | |
| | 147 ; | NORMALIZE Y |
| | 148 ; | |
| 0003 CDD302 C | 149 | CALL NORMY |
| | 150 ; | |
| | 151 ; | IF MANTISSA X = 0 THEN |
| | 152 ; | |
| 0006 210000 D | 153 | LXI H,X |
| 0009 CD5903 C | 154 | CALL TEST0 |
| 000C C21500 C | 155 | JNZ ADD1 |
| | 156 ; | |
| | 157 ; |   X <- Y |
| | 158 ; | |
| 000F CD9602 C | 159 | CALL DNY |
| 0012 C3D500 C | 160 | JMP ADD12 |
| | 161 ; | |
| | 162 ; | ELSE |
| | 163 ; |   IF MANTISSA Y <> 0 THEN |
| | 164 ; | |
| 0015 210600 D | 165 ADD1: | LXI H,Y |
| 0018 CD5903 C | 166 | CALL TEST0 |
| 001B CAD500 C | 167 | JZ ADD12 |
| | 168 ; | |
| | 169 ; |   DO WHILE EXPONENT X <> EXPONENT Y |
| | 170 ; | |
| 001E 210A00 D | 171 ADD2: | LXI H,EXPY |
| 0021 7E | 172 | MOV A,M |
| 0022 210400 D | 173 | LXI H,EXPX |
| 0025 96 | 174 | SUB M |
| 0026 CA4600 C | 175 | JZ ADD4 |
| | 176 ; | |
| | 177 ; |   IF EXPONENT X < EXPONENT Y THEN |
| | 178 ; | |

| LOC OBJ | | LINE | SOURCE STATEMENT | |
|---|---|---|---|---|
| 0029 FA3900 | C | 179 | JM | ADD3 |
| | | 180 ; | | |
| | | 181 ; | SHIFT MANTISSA X RIGHT ONE DIGIT | |
| | | 182 ; | | |
| 002C 210000 | D | 183 | LXI | H,X |
| 002F CD2D03 | C | 184 | CALL | SHIFTR |
| | | 185 ; | | |
| | | 186 ; | INCREMENT EXPONENT X | |
| | | 187 ; | | |
| 0032 210400 | D | 188 | LXI | H,EXPX |
| 0035 34 | | 189 | INR | M |
| 0036 C31E00 | C | 190 | JMP | ADD2 |
| | | 191 ; | | |
| | | 192 ; | ELSE | |
| | | 193 ; | SHIFT MANTISSA Y RIGHT ONE DIGIT | |
| | | 194 ; | | |
| 0039 210600 | D | 195 ADD3: | LXI | H,Y |
| 003C CD2D03 | C | 196 | CALL | SHIFTR |
| | | 197 ; | | |
| | | 198 ; | INCREMENT EXPONENT Y | |
| | | 199 ; | | |
| 003F 210A00 | D | 200 | LXI | H,EXPY |
| 0042 34 | | 201 | INR | M |
| 0043 C31E00 | C | 202 | JMP | ADD2 |
| | | 203 ; | | |
| | | 204 ; | END | |
| | | 205 ; | END | |
| | | 206 ; | | |
| | | 207 ; | SHIFT MANTISSA X RIGHT ONE DIGIT | |
| | | 208 ; | | |
| 0046 210000 | D | 209 ADD4: | LXI | H,X |
| 0049 CD2D03 | C | 210 | CALL | SHIFTR |
| | | 211 ; | | |
| | | 212 ; | INCREMENT EXPONENT X | |
| | | 213 ; | | |
| 004C 210400 | D | 214 | LXI | H,EXPX |
| 004F 34 | | 215 | INR | M |
| | | 216 ; | | |
| | | 217 ; | SHIFT MANTISSA Y RIGHT ONE DIGIT | |
| | | 218 ; | | |
| 0050 210600 | D | 219 | LXI | H,Y |
| 0053 CD2D03 | C | 220 | CALL | SHIFTR |
| | | 221 ; | | |
| | | 222 ; | INCREMENT EXPONENT Y | |
| | | 223 ; | | |
| 0056 210A00 | D | 224 | LXI | H,EXPY |
| 0059 34 | | 225 | INR | M |
| | | 226 ; | | |
| | | 227 ; | IF SIGN X = SIGN Y THEN | |
| | | 228 ; | | |
| 005A 210B00 | D | 229 | LXI | H,SIGNY |
| 005D 7E | | 230 | MOV | A,M |
| 005E 210500 | D | 231 | LXI | H,SIGNX |
| 0061 AE | | 232 | XRA | M |
| 0062 C27B00 | C | 233 | JNZ | ADD6 |
| | | 234 ; | | |
| | | 235 ; | MANTISSA X = MANTISSA Y + MANTISSA X | |
| | | 236 ; | | |
| 0065 110600 | D | 237 | LXI | D,Y |
| 0068 210000 | D | 238 | LXI | H,X |
| 006B 0E04 | | 239 | MVI | C,4 |

```
LOC  OBJ          LINE       SOURCE STATEMENT

006D AF           240            XRA    A
006E 1A           241 ADD5:      LDAX   D
006F 8E           242            ADC    M
0070 27           243            DAA
0071 77           244            MOV    M,A
0072 13           245            INX    D
0073 23           246            INX    H
0074 0D           247            DCR    C
0075 C26E00  C    248            JNZ    ADD5
0078 C3B900  C    249            JMP    ADD10
                  250 ;
                  251 ;          ELSE
                  252 ;            IF MANTISSA X <= MANTISSA Y THEN
                  253 ;
007B CD8402  C    254 ADD6:      CALL   CMPR
007E DAA000  C    255            JC     ADD8;
                  256 ;
                  257 ;            MANTISSA X = MANTISSA Y - MANTISSA X
                  258 ;
0081 110600  D    259            LXI    D,Y
0084 210000  D    260            LXI    H,X
0087 0E04         261            MVI    C,4
0089 37           262            STC
008A 3E99         263 ADD7:      MVI    A,99H
008C CE00         264            ACI    0
008E 96           265            SUB    M
008F EB           266            XCHG
0090 86           267            ADD    M
0091 EB           268            XCHG
0092 27           269            DAA
0093 77           270            MOV    M,A
0094 13           271            INX    D
0095 23           272            INX    H
0096 0D           273            DCR    C
0097 C28A00  C    274            JNZ    ADD7
                  275 ;
                  276 ;          CHANGE SIGN X
                  277 ;
009A CD6E02  C    278            CALL   CHGSNX
009D C3B900  C    279            JMP    ADD10
                  280 ;
                  281 ;          ELSE
                  282 ;            MANTISSA X = MANTISSA X - MANTISSA Y
                  283 ;
00A0 110600  D    284 ADD8:      LXI    D,Y
00A3 210000  D    285            LXI    H,X
00A6 0E04         286            MVI    C,4
00A8 37           287            STC
00A9 3E99         288 ADD9:      MVI    A,99H
00AB CE00         289            ACI    0
00AD EB           290            XCHG
00AE 96           291            SUB    M
00AF EB           292            XCHG
00B0 86           293            ADD    M
00B1 27           294            DAA
00B2 77           295            MOV    M,A
00B3 13           296            INX    D
00B4 23           297            INX    H
00B5 0D           298            DCR    C
00B6 C2A900  C    299            JNZ    ADD9
                  300 ;
```

```
LOC  OBJ          LINE     SOURCE STATEMENT

301 ;           END
                  302 ;         END
                  303 ;       IF MANTISSA X = 0 THEN
                  304 ;
00B9 210000  D    305 ADD10: LXI   H,X
00BC CD5903  C    306         CALL  TEST0
00BF C2CF00  C    307         JNZ   ADD11
                  308 ;
                  309 ;         SIGN X = POSITIVE
                  310 ;
00C2 210500  D    311         LXI   H,SIGNX
00C5 3600         312         MVI   M,0
                  313 ;
                  314 ;         EXPONENT X = 0
                  315 ;
00C7 210400  D    316         LXI   H,EXPX
00CA 3600         317         MVI   M,0
00CC C3D500  C    318         JMP   ADD12
                  319 ;
                  320 ;       ELSE
                  321 ;         NORMALIZE X
                  322 ;
00CF CDB802  C    323 ADD11: CALL  NORMX
                  324 ;
                  325 ;         ROUND X TO SIX DIGITS
                  326 ;
00D2 CDEE02  C    327         CALL  RND6
                  328 ;
                  329 ;         END
                  330 ;       END
                  331 ;     END
                  332 ;     Y <- Z
                  333 ;     Z <- T
                  334 ;
00D5 CDA702  C    335 ADD12: CALL  DNZT
                  336 ;
00D8 C9           337         RET
                  338 ;
                  339 ;****************************************************************
                  340 ;
                  341 ;   SUBTRACTION ROUTINE
                  342 ;
                  343 ;   CHANGE SIGN X
                  344 ;   JUMP TO ADD ROUTINE
                  345 ;
                  346 ;
00D9 CD6E02  C    347 BCDSUB: CALL CHGSNX
00DC C30000  C    348         JMP   BCDADD
                  349 ;
                  350 ;****************************************************************
                  351 ;
                  352 ;   MULTIPLICATION ROUTINE
                  353 ;
                  354 ;   NORMALIZE X
                  355 ;   NORMALIZE Y
                  356 ;   IF MANTISSA Y = 0 THEN
                  357 ;     X = 0
                  358 ;   ELSE
                  359 ;     IF MANTISSA X <> 0 THEN
                  360 ;       IF SIGN X = SIGN Y THEN
                  361 ;         SIGN X = POSITIVE
```

```
LOC  OBJ          LINE      SOURCE STATEMENT

362 ;             ELSE
                  363 ;               SIGN X = NEGATIVE
                  364 ;             END
                  365 ;             EXPONENT X = EXPONENT Y + EXPONENT X
                  366 ;             SHIFT MANTISSA Y RIGHT ONE DIGIT
                  367 ;             RESULT = 0
                  368 ;             DIGIT COUNT = 6
                  369 ;             DO UNTIL DIGIT COUNT = 0
                  370 ;               DO WHILE DIGIT 2 OF MANTISSA X > 0
                  371 ;                 RESULT = RESULT + MANTISSA Y
                  372 ;                 DECREMENT DIGIT 2 OF MANTISSA X
                  373 ;               END
                  374 ;               DECREMENT DIGIT COUNT
                  375 ;               IF DIGIT COUNT > 0 THEN
                  376 ;                 SHIFT RESULT RIGHT ONE DIGIT
                  377 ;                 SHIFT MANTISSA X RIGHT ONE DIGIT
                  378 ;               END
                  379 ;             END
                  380 ;             RESULT -> MANTISSA X
                  381 ;             NORMALIZE X
                  382 ;             ROUND X TO SIX DIGITS
                  383 ;           END
                  384 ;         END
                  385 ;         Y <- Z
                  386 ;         Z <- T
                  387 ;
                  388 ;
                  389 ;         NORMALIZE X
                  390 ;
00DF CDB802   C   391 LCDMUL: CALL  NORMX
                  392 ;
                  393 ;         NORMALIZE Y
                  394 ;
00E2 CDD302   C   395           CALL  NORMY
                  396 ;
                  397 ;         IF MANTISSA Y = 0 THEN
                  398 ;
00E5 210600   D   399           LXI   H,Y
00E8 CD5903   C   400           CALL  TEST0
00EB C2F400   C   401           JNZ   MUL1
                  402 ;
                  403 ;           X = 0
                  404 ;
00EE CD6002   C   405           CALL  CLEARX
00F1 C36201   C   406           JMP   MUL8
                  407 ;
                  408 ;         ELSE
                  409 ;           IF MANTISSA X <> 0 THEN
                  410 ;
00F4 210000   D   411 MUL1:   LXI   H,X
00F7 CD5903   C   412           CALL  TEST0
00FA CA6201   C   413           JZ    MUL8
                  414 ;
                  415 ;             IF SIGN X = SIGN Y THEN
                  416 ;
00FD 210B00   D   417           LXI   H,SIGNY
0100 7E           418           MOV   A,M
0101 210500   D   419           LXI   H,SIGNX
0104 AE           420           XRA   M
0105 C20D01   C   421           JNZ   MUL2
                  422 ;
```

```
LOC  OBJ         LINE      SOURCE STATEMENT

423 ;              SIGN X = POSITIVE
                 424 ;
0108 3600        425       MVI     M,0
010A C30F01  C   426       JMP     MUL3
                 427 ;
                 428 ;          ELSE
                 429 ;              SIGN X = NEGATIVE
                 430 ;
010D 3680        431 MUL2: MVI     M,80H
                 432 ;
                 433 ;          END
                 434 ;          EXPONENT X = EXPONENT Y + EXPONENT X
                 435 ;
010F 210A00  D   436 MUL3: LXI     H,EXPY
0112 7E          437       MOV     A,M
0113 210400  D   438       LXI     H,EXPX
0116 86          439       ADD     M
0117 77          440       MOV     M,A
                 441 ;
                 442 ;          SHIFT MANTISSA Y RIGHT ONE DIGIT
                 443 ;
0118 210600  D   444       LXI     H,Y
011B CD2D03  C   445       CALL    SHIFTR
                 446 ;
                 447 ;          RESULT = 0
                 448 ;
011E CD7602  C   449       CALL    CLEARS
                 450 ;
                 451 ;          DIGIT COUNT = 6
                 452 ;
0121 0606        453       MVI     B,6
                 454 ;
                 455 ;          DO UNTIL DIGIT COUNT = 0
                 456 ;              DO WHILE DIGIT 2 OF MANTISSA X > 0
                 457 ;
0123 210100  D   458 MUL4: LXI     H,X+1
0126 7E          459       MOV     A,M
0127 E60F        460       ANI     0FH
0129 CA4601  C   461       JZ      MUL6
                 462 ;
                 463 ;              RESULT = RESULT + MANTISSA Y
                 464 ;
012C 110600  D   465       LXI     D,Y
012F 211800  D   466       LXI     H,S
0132 0E04        467       MVI     C,4
0134 AF          468       XRA     A
0135 1A          469 MUL5: LDAX    D
0136 8E          470       ADC     M
0137 27          471       DAA
0138 77          472       MOV     M,A
0139 13          473       INX     D
013A 23          474       INX     H
013B 0D          475       DCR     C
013C C23501  C   476       JNZ     MUL5
                 477 ;
                 478 ;              DECREMENT DIGIT 2 OF MANTISSA X
                 479 ;
013F 210100  D   480       LXI     H,X+1
0142 35          481       DCR     M
0143 C32301  C   482       JMP     MUL4
                 483 ;
                 484 ;          END;
```

| LOC OBJ | | LINE | SOURCE STATEMENT | | |
|---|---|---|---|---|---|
| | | 485 ; | | DECREMENT DIGIT COUNT | |
| | | 486 ; | | | |
| 0146 05 | | 487 MUL6: | DCR | B | |
| | | 488 ; | | | |
| | | 489 ; | | IF DIGIT COUNT > 0 THEN | |
| | | 490 ; | | | |
| 0147 CA5901 | C | 491 | JZ | MUL7 | |
| | | 492 ; | | | |
| | | 493 ; | | SHIFT RESULT RIGHT ONE DIGIT | |
| | | 494 ; | | | |
| 014A 211800 | D | 495 | LXI | H,S | |
| 014D CD2D03 | C | 496 | CALL | SHIFTR | |
| | | 497 ; | | | |
| | | 498 ; | | SHIFT MANTISSA X RIGHT ONE DIGIT | |
| | | 499 ; | | | |
| 0150 210000 | D | 500 | LXI | H,X | |
| 0153 CD2D03 | C | 501 | CALL | SHIFTR | |
| 0156 C32301 | C | 502 | JMP | MUL4 | |
| | | 503 ; | | | |
| | | 504 ; | END | | |
| | | 505 ; | END | | |
| | | 506 ; | RESULT -> MANTISSA X | | |
| | | 507 ; | | | |
| 0159 CD4803 | C | 508 MUL7: | CALL | STOX | |
| | | 509 ; | | | |
| | | 510 ; | NORMALIZE X | | |
| | | 511 ; | | | |
| 015C CDB802 | C | 512 | CALL | NORMX | |
| | | 513 ; | | | |
| | | 514 ; | ROUND X TO SIX DIGITS | | |
| | | 515 ; | | | |
| 015F CDEE02 | C | 516 | CALL | RND6 | |
| | | 517 ; | | | |
| | | 518 ; | END | | |
| | | 519 ; | END | | |
| | | 520 ; | Y <- Z | | |
| | | 521 ; | Z <- T | | |
| | | 522 ; | | | |
| 0162 CDA702 | C | 523 MUL8: | CALL | DNZT | |
| | | 524 ; | | | |
| 0165 C9 | | 525 | RET | | |
| | | 526 ; | | | |
| | | 527 ;**************************************************************** | | | |
| | | 528 ; | | | |
| | | 529 ; | DIVISION ROUTINE | | |
| | | 530 ; | | | |
| | | 531 ; | NORMALIZE X | | |
| | | 532 ; | NORMALIZE Y | | |
| | | 533 ; | RESET DIVISION BY 0 FLAG | | |
| | | 534 ; | IF MANTISSA Y = 0 THEN | | |
| | | 535 ; |   X = 0 | | |
| | | 536 ; | ELSE | | |
| | | 537 ; |   IF MANTISSA X = 0 THEN | | |
| | | 538 ; |     SET DIVISION BY 0 FLAG | | |
| | | 539 ; |   ELSE | | |
| | | 540 ; |     IF SIGN X = SIGN Y THEN | | |
| | | 541 ; |       SIGN X = POSITIVE | | |
| | | 542 ; |     ELSE | | |
| | | 543 ; |       SIGN X = NEGATIVE | | |
| | | 544 ; |     END | | |
| | | 545 ; |     EXPONENT X = (EXPONENT Y - EXPONENT X) + 1 | | |

```
LOC  OBJ         LINE       SOURCE STATEMENT

546 ;          SHIFT MANTISSA Y RIGHT ONE DIGIT
                 547 ;          SHIFT MANTISSA X RIGHT ONE DIGIT
                 548 ;          QUOTIENT = 0
                 549 ;          DIGIT COUNT = 8
                 550 ;          DO UNTIL DIGIT COUNT = 0
                 551 ;             DO WHILE MANTISSA X <= MANTISSA Y
                 552 ;                MANTISSA Y = MANTISSA Y - MANTISSA X
                 553 ;                INCREMENT DIGIT 0 OF QUOTIENT
                 554 ;             END
                 555 ;             DECREMENT DIGIT COUNT
                 556 ;             IF DIGIT COUNT > 0 THEN
                 557 ;                SHIFT QUOTIENT LEFT ONE DIGIT
                 558 ;                SHIFT MANTISSA Y LEFT ONE DIGIT
                 559 ;             END
                 560 ;          END
                 561 ;          QUOTIENT -> MANTISSA X
                 562 ;          NORMALIZE X
                 563 ;          ROUND X TO SIX DIGITS
                 564 ;       END
                 565 ;    END
                 566 ;    Y <- Z
                 567 ;    Z <- T
                 568 ;
                 569 ;
                 570 ;    NORMALIZE X
                 571 ;
0166 CDB802  C   572 BCDDIV: CALL    NORMX
                 573 ;
                 574 ;    NORMALIZE Y
                 575 ;
0169 CDD302  C   576       CALL    NORMY
                 577 ;
                 578 ;    RESET DIVISION BY 0 FLAG
                 579 ;
016C 211C00  D   580       LXI     H,DIV0
016F 3600        581       MVI     M,0
                 582 ;
                 583 ;    IF MANTISSA Y = 0 THEN
                 584 ;
0171 210600  D   585       LXI     H,Y
0174 CD5903  C   586       CALL    TEST0
0177 C28001  C   587       JNZ     DIV1
                 588 ;
                 589 ;       X = 0
                 590 ;
017A CD6002  C   591       CALL    CLEARX
017D C30302  C   592       JMP     DIV10
                 593 ;
                 594 ;    ELSE
                 595 ;       IF MANTISSA X = 0 THEN
                 596 ;
0180 210000  D   597 DIV1: LXI     H,X
0183 CD5903  C   598       CALL    TEST0
0186 C29101  C   599       JNZ     DIV2
                 600 ;
                 601 ;          SET DIVISION BY ZERO FLAG
                 602 ;
0189 211C00  D   603       LXI     H,DIV0
018C 36FF        604       MVI     M,0FFH
018E C30302  C   605       JMP     DIV10
                 606 ;
```

```
LOC  OBJ           LINE       SOURCE STATEMENT

607 ;          ELSE
                   608 ;             IF SIGN X = SIGN Y THEN
                   609 ;
0191 210B00   D    610 DIV2:   LXI    H,SIGNY
0194 7E            611         MOV    A,M
0195 210500   D    612         LXI    H,SIGNX
0198 AE            613         XRA    M
0199 C2A101   C    614         JNZ    DIV3
                   615 ;
                   616 ;             SIGN X = POSITIVE
                   617 ;
019C 3600          618         MVI    M,0
019E C3A301   C    619         JMP    DIV4
                   620 ;
                   621 ;          ELSE
                   622 ;             SIGN X = NEGATIVE
                   623 ;
01A1 3680          624 DIV3:   MVI    M,80H
                   625 ;
                   626 ;          END
                   627 ;          EXPONENT X = (EXPONENT Y - EXPONENT X) + 1
                   628 ;
01A3 210A00   D    629 DIV4:   LXI    H,EXPY
01A6 7E            630         MOV    A,M
01A7 210400   D    631         LXI    H,EXPX
01AA 96            632         SUB    M
01AB 3C            633         INR    A
01AC 77            634         MOV    M,A
                   635 ;
                   636 ;          SHIFT MANTISSA Y RIGHT ONE DIGIT
                   637 ;
01AD 210600   D    638         LXI    H,Y
01B0 CD2D03   C    639         CALL   SHIFTR
                   640 ;
                   641 ;          SHIFT MANTISSA X RIGHT ONE DIGIT
                   642 ;
01B3 210000   D    643         LXI    H,X
01B6 CD2D03   C    644         CALL   SHIFTR
                   645 ;
                   646 ;          CLEAR QUOTIENT
                   647 ;
01B9 CD7602   C    648         CALL   CLEARS
                   649 ;
                   650 ;          DIGIT COUNT = 8
                   651 ;
01BC 0608          652         MVI    B,8
                   653 ;
                   654 ;          DO UNTIL DIGIT COUNT = 0
                   655 ;             DO WHILE MANTISSA X <= MANTISSA Y
                   656 ;
01BE CD3402   C    657 DIV5:   CALL   CMPR
01C1 CAC701   C    658         JZ     DIV6
01C4 DAE701   C    659         JC     DIV8
                   660 ;
                   661 ;             MANTISSA Y = MANTISSA Y - MANTISSA X
                   662 ;
01C7 110600   D    663 DIV6:   LXI    D,Y
01CA 210000   D    664         LXI    H,X
01CD 0E04          665         MVI    C,4
01CF 37            666         STC
01D0 3E99          667 DIV7:   MVI    A,99H
```

```
LOC  OBJ         LINE       SOURCE STATEMENT

01D2 CE00        668        ACI     0
01D4 96          669        SUB     M
01D5 EB          670        XCHG
01D6 86          671        ADD     M
01D7 27          672        DAA
01D8 77          673        MOV     M,A
01D9 EB          674        XCHG
01DA 13          675        INX     D
01DB 23          676        INX     H
01DC 0D          677        DCR     C
01DD C2D001  C   678        JNZ     DIV7
                 679 ;
                 680 ;              INCREMENT DIGIT 0 OF QUOTIENT
                 681 ;
01E0 211800  D   682        LXI     H,S
01E3 34          683        INR     M
01E4 C3BE01  C   684        JMP     DIV5
                 685 ;
                 686 ;              END
                 687 ;              DECREMENT DIGIT COUNT
                 688 ;
01E7 05          689 DIV8:  DCR     B
                 690 ;
                 691 ;              IF DIGIT COUNT > 0 THEN
                 692 ;
01E8 CAFA01  C   693        JZ      DIV9
                 694 ;
                 695 ;              SHIFT QUOTIENT LEFT ONE DIGIT
                 696 ;
01EB 211800  D   697        LXI     H,S
01EE CD1503  C   698        CALL    SHIFTL
                 699 ;
                 700 ;              SHIFT MANTISSA Y LEFT ONE DIGIT
                 701 ;
01F1 210600  D   702        LXI     H,Y
01F4 CD1503  C   703        CALL    SHIFTL
01F7 C3BE01  C   704        JMP     DIV5
                 705 ;
                 706 ;          END
                 707 ;        END
                 708 ;        QUOTIENT -> MANTISSA X
                 709 ;
01FA CD4803  C   710 DIV9:  CALL    STOX
                 711 ;
                 712 ;        NORMALIZE X
                 713 ;
01FD CDB802  C   714        CALL    NORMX
                 715 ;
                 716 ;        ROUND X TO SIX DIGITS
                 717 ;
0200 CDEE02  C   718        CALL    RND6
                 719 ;
                 720 ;      END
                 721 ;    END
                 722 ;    Y <- Z
                 723 ;    Z <- T
                 724 ;
0203 CDA702  C   725 DIV10: CALL    DNZT
                 726 ;
0206 C9         727         RET
                 728 ;
```

```
LOC  OBJ         LINE       SOURCE STATEMENT

729 ;************************************************************
                 730 ;
                 731 ;
                 732 ;         Z -> T
                 733 ;         Y -> Z
                 734 ;         X -> Y
                 735 ;         SIX DIGIT VARIABLE -> X
                 736 ;
                 737 ;         REGISTER PAIR BC HOLDS VARIABLE ADDRESS
                 738 ;
                 739 ;
0207 C5          740 LOAD:    PUSH    B
0208 011100  D   741          LXI     B,SIGNZ
020B 111700  D   742          LXI     D,SIGNT
020E 2E12        743          MVI     L,18
0210 0A          744 LOAD1:   LDAX    B
0211 12          745          STAX    D
0212 0B          746          DCX     B
0213 1B          747          DCX     D
0214 2D          748          DCR     L
0215 C21002  C   749          JNZ     LOAD1
0218 C1          750          POP     B
0219 210000  D   751          LXI     H,X
021C 3600        752          MVI     M,0
021E 23          753          INX     H
021F 1E05        754          MVI     E,5
0221 0A          755 LOAD2:   LDAX    B
0222 77          756          MOV     M,A
0223 03          757          INX     B
0224 23          758          INX     H
0225 1D          759          DCR     E
0226 C22102  C   760          JNZ     LOAD2
0229 C9          761          RET
                 762 ;
                 763 ;************************************************************
                 764 ;
                 765 ;         SIX DIGIT VARIABLE <- X
                 766 ;
                 767 ;         REGISTER PAIR BC HOLDS VARIABLE ADDRESS
                 768 ;
                 769 ;
022A 210000  D   770 STORE:   LXI     H,X
022D 23          771          INX     H
022E 1E05        772          MVI     E,5
0230 7E          773 ST1:     MOV     A,M
0231 02          774          STAX    B
0232 03          775          INX     B
0233 23          776          INX     H
0234 1D          777          DCR     E
0235 C23002  C   778          JNZ     ST1
0238 C9          779          RET
                 780 ;
                 781 ;************************************************************
                 782 ;
                 783 ;         FIX DECIMAL POINT OF STACK REGISTER X
                 784 ;
                 785 ;         DO WHILE EXPONENT X <> REGISTER C
                 786 ;            IF EXPONENT X < REGISTER C THEN
                 787 ;               SHIFT MANTISSA X RIGHT ONE DIGIT
                 788 ;               INCREMENT EXPONENT X
                 789 ;            ELSE
```

```
LOC  OBJ        LINE        SOURCE STATEMENT

790 ;           SHIFT MANTISSA X LEFT ONE DIGIT
                791 ;           DECREMENT EXPONENT X
                792 ;        END
                793 ;     END
                794 ;
                795 ;
                796 ;     DO WHILE EXPONENT X <> REGISTER C
                797 ;
0239 79         798 FIX:   MOV    A,C
023A 210400  D  799         LXI    H,EXPX
023D 96         800         SUB    M
023E C8         801         RZ
                802 ;
                803 ;        IF EXPONENT X < REGISTER C THEN
                804 ;
023F FA5102  C  805         JM     FIX1
                806 ;
                807 ;           SHIFT MANTISSA X RIGHT ONE DIGIT
                808 ;
0242 210000  D  809         LXI    H,X
0245 C5         810         PUSH   B
0246 CD2D03  C  811         CALL   SHIFTR
0249 C1         812         POP    B
                813 ;
                814 ;           INCREMENT EXPONENT X
                815 ;
024A 210400  D  816         LXI    H,EXPX
024D 34         817         INR    M
024E C33902  C  818         JMP    FIX
                819 ;
                820 ;        ELSE
                821 ;           SHIFT MANTISSA X LEFT ONE DIGIT
                822 ;
0251 210000  D  823 FIX1:  LXI    H,X
0254 C5         824         PUSH   B
0255 CD1503  C  825         CALL   SHIFTL
0258 C1         826         POP    B
                827 ;
                828 ;           DECREMENT EXPONENT X
                829 ;
0259 210400  D  830         LXI    H,EXPX
025C 35         831         DCR    M
025D C33902  C  832         JMP    FIX
                833 ;
                834 ;        END
                835 ;     END
                836 ;
                837 ;;****************************************************************
                838 ;
                839 ;     X = 0
                840 ;
0260 210000  D  841 CLEARX: LXI   H,X
0263 0E06       842         MVI    C,6
0265 3E00       843         MVI    A,0
0267 77         844 CLRX1: MOV    M,A
0268 23         845         INX    H
0269 0D         846         DCR    C
026A C26702  C  847         JNZ    CLRX1
026D C9         848         RET
                849 ;
                850 ;****************************************************************
```

```
LOC  OBJ         LINE        SOURCE STATEMENT

851 ;
                 852 ;       CHANGE SIGN X
                 853 ;
                 854 ;       IF SIGN X = POSITIVE THEN
                 855 ;          SIGN X = NEGATIVE
                 856 ;       ELSE
                 857 ;          SIGN X = POSITIVE
                 858 ;       END
                 859 ;
                 860 ;
026E 210500   D  861 CHGSNX: LXI    H,SIGNX
0271 7E          862         MOV    A,M
0272 EE80        863         XRI    80H
0274 77          864         MOV    M,A
0275 C9          865         RET
                 866 ;
                 867 ;
                 868 ;****************************************************************
                 869 ;
                 870 ;       S = 0
                 871 ;
0276 211800   D  872 CLEARS: LXI    H,S
0279 0E04        873         MVI    C,4
027B 3E00        874         MVI    A,0
027D 77          875 CLRS1:  MOV    M,A
027E 23          876         INX    H
027F 0D          877         DCR    C
0280 C27D02   C  878         JNZ    CLRS1
0283 C9          879         RET
                 880 ;
                 881 ;****************************************************************
                 882 ;
                 883 ;       COMPARE MANTISSA X TO MANTISSA Y
                 884 ;
                 885 ;       RETURN ZERO AND NO CARRY IF X = Y
                 886 ;       RETURN NOT ZERO AND NO CARRY IF X < Y
                 887 ;       RETURN NOT ZERO AND CARRY IF X > Y
                 888 ;
                 889 ;
0284 110900   D  890 CMPR:   LXI    D,Y+3
0287 210300   D  891         LXI    H,X+3
028A 0E04        892         MVI    C,4
028C 1A          893 CMPR1:  LDAX   D
028D 96          894         SUB    M
028E C0          895         RNZ
028F 1B          896         DCX    D
0290 2B          897         DCX    H
0291 0D          898         DCR    C
0292 C28C02   C  899         JNZ    CMPR1
0295 C9          900         RET
                 901 ;
                 902 ;****************************************************************
                 903 ;
                 904 ;       X <- Y
                 905 ;
0296 010600   D  906 DNY:    LXI    B,Y
0299 110000   D  907         LXI    D,X
029C 2E06        908         MVI    L,6
029E 0A          909 DNY1:   LDAX   B
029F 12          910         STAX   D
02A0 03          911         INX    B
```

```
LOC  OBJ        LINE       SOURCE STATEMENT

02A1 13          912       INX    D
02A2 2D          913       DCR    L
02A3 C29E02  C   914       JNZ    DNY1
02A6 C9          915       RET
                 916 ;
                 917 ;****************************************************************
                 918 ;
                 919 ;       Y <- Z
                 920 ;       Z <- T
                 921 ;
                 922 ;
02A7 010C00  D   923 DNZT:  LXI    B,Z
02AA 110600  D   924        LXI    D,Y
02AD 2E0C        925        MVI    L,12
02AF 0A          926 DNZT1: LDAX   B
02B0 12          927        STAX   D
02B1 03          928        INX    B
02B2 13          929        INX    D
02B3 2D          930        DCR    L
02B4 C2AF02  C   931        JNZ    DNZT1
02B7 C9          932        RET
                 933 ;
                 934 ;****************************************************************
                 935 ;
                 936 ;       NORMALIZE X
                 937 ;
                 938 ;       IF MANTISSA X <> 0 THEN
                 939 ;          DO WHILE THE MOST SIGNIFICANT DIGIT OF X = 0
                 940 ;             SHIFT MANTISSA X LEFT ONE DIGIT
                 941 ;             DECREMENT EXPONENT X
                 942 ;          END
                 943 ;       END
                 944 ;
                 945 ;
02B8 210000  D   946 NORMX: LXI    H,X
02BB CD5903  C   947        CALL   TEST0
02BE C8          948        RZ
02BF 210300  D   949 NORMX1: LXI   H,X+3
02C2 3EF0        950        MVI    A,0F0H
02C4 A6          951        ANA    M
02C5 C0          952        RNZ
02C6 210000  D   953        LXI    H,X
02C9 CD1503  C   954        CALL   SHIFTL
02CC 210400  D   955        LXI    H,EXPX
02CF 35          956        DCR    M
02D0 C3BF02  C   957        JMP    NORMX1
                 958 ;
                 959 ;****************************************************************
                 960 ;
                 961 ;       NORMALIZE Y
                 962 ;
                 963 ;       IF MANTISSA Y <> 0 THEN
                 964 ;          DO WHILE THE MOST SIGNIFICANT DIGIT OF Y = 0
                 965 ;             SHIFT MANTISSA Y LEFT ONE DIGIT
                 966 ;             DECREMENT EXPONENT Y
                 967 ;          END
                 968 ;       END
                 969 ;
                 970 ;
02D3 210600  D   971 NORMY: LXI    H,Y
02D6 CD5903  C   972        CALL   TEST0
```

| LOC | OBJ | | LINE | SOURCE STATEMENT | |
|---|---|---|---|---|---|
| 02D9 | C8 | | 973 | RZ | |
| 02DA | 210900 | D | 974 NORMY1: | LXI | H,Y+3 |
| 02DD | 3EF0 | | 975 | MVI | A,0F0H |
| 02DF | A6 | | 976 | ANA | M |
| 02E0 | C0 | | 977 | RNZ | |
| 02E1 | 210600 | D | 978 | LXI | H,Y |
| 02E4 | CD1503 | C | 979 | CALL | SHIFTL |
| 02E7 | 210A00 | D | 980 | LXI | H,EXPY |
| 02EA | 35 | | 981 | DCR | M |
| 02EB | C3DA02 | C | 982 | JMP | NORMY1 |

```
983 ;
984 ;****************************************************************
985 ;
986 ;    ROUND X TO SIX DIGITS
987 ;
988 ;    SHIFT MANTISSA X RIGHT ONE DIGIT
989 ;    INCREMENT EXPONENT X
990 ;    ADD 00000005 TO MANTISSA X
991 ;    NORMALIZE X
992 ;    LEAST SIGNIFICANT BYTE OF MANTISSA X = 0
993 ;
994 ;
```

| LOC | OBJ | | LINE | SOURCE STATEMENT | |
|---|---|---|---|---|---|
| 02EE | 210000 | D | 995 RND6: | LXI | H,X |
| 02F1 | CD2D03 | C | 996 | CALL | SHIFTR |
| 02F4 | 210400 | D | 997 | LXI | H,EXPX |
| 02F7 | 34 | | 998 | INR | M |
| 02F8 | 210000 | D | 999 | LXI | H,X |
| 02FB | 0E03 | | 1000 | MVI | C,3 |
| 02FD | 3E05 | | 1001 | MVI | A,5 |
| 02FF | 86 | | 1002 | ADD | M |
| 0300 | 27 | | 1003 | DAA | |
| 0301 | 77 | | 1004 | MOV | M,A |
| 0302 | 23 | | 1005 RND61: | INX | H |
| 0303 | 7E | | 1006 | MOV | A,M |
| 0304 | CE00 | | 1007 | ACI | 0 |
| 0306 | 27 | | 1008 | DAA | |
| 0307 | 77 | | 1009 | MOV | M,A |
| 0308 | 0D | | 1010 | DCR | C |
| 0309 | C20203 | C | 1011 | JNZ | RND61 |
| 030C | CDB802 | C | 1012 | CALL | NORMX |
| 030F | 210000 | D | 1013 | LXI | H,X |
| 0312 | 3600 | | 1014 | MVI | M,0 |
| 0314 | C9 | | 1015 | RET | |

```
1016 ;
1017 ;****************************************************************
1018 ;
1019 ;    SHIFT MANTISSA LEFT ONE DIGIT
1020 ;
1021 ;    REGISTER PAIR HL HOLDS MANTISSA ADDRESS
1022 ;
1023 ;
```

| LOC | OBJ | LINE | SOURCE STATEMENT | |
|---|---|---|---|---|
| 0315 | 0E04 | 1024 SHIFTL: | MVI | C,4 |
| 0317 | 1600 | 1025 | MVI | D,0 |
| 0319 | 7E | 1026 SL1: | MOV | A,M |
| 031A | 07 | 1027 | RLC | |
| 031B | 07 | 1028 | RLC | |
| 031C | 07 | 1029 | RLC | |
| 031D | 07 | 1030 | RLC | |
| 031E | 5F | 1031 | MOV | E,A |
| 031F | E6F0 | 1032 | ANI | 0F0H |

```
LOC  OBJ        LINE       SOURCE STATEMENT

0321 B2          1033        ORA    D
0322 77          1034        MOV    M,A
0323 7B          1035        MOV    A,E
0324 E60F        1036        ANI    0FH
0326 57          1037        MOV    D,A
0327 23          1038        INX    H
0328 0D          1039        DCR    C
0329 C21903  C   1040        JNZ    SL1
032C C9          1041        RET
                 1042 ;
                 1043 ;************************************************************
                 1044 ;
                 1045 ;     SHIFT MANTISSA RIGHT ONE DIGIT
                 1046 ;
                 1047 ;     REGISTER PAIR HL HOLDS MANTISSA ADDRESS
                 1048 ;
                 1049 ;
032D 23          1050 SHIFTR: INX  H
032E 23          1051        INX    H
032F 23          1052        INX    H
0330 0E04        1053        MVI    C,4
0332 1600        1054        MVI    D,0
0334 7E          1055 SR1:   MOV    A,M
0335 0F          1056        RRC
0336 0F          1057        RRC
0337 0F          1058        RRC
0338 0F          1059        RRC
0339 5F          1060        MOV    E,A
033A E60F        1061        ANI    0FH
033C B2          1062        ORA    D
033D 77          1063        MOV    M,A
033E 7B          1064        MOV    A,E
033F E6F0        1065        ANI    0F0H
0341 57          1066        MOV    D,A
0342 2B          1067        DCX    H
0343 0D          1068        DCR    C
0344 C23403  C   1069        JNZ    SR1
0347 C9          1070        RET
                 1071 ;
                 1072 ;************************************************************
                 1073 ;
                 1074 ;     SCRATCH -> MANTISSA X
                 1075 ;
0348 011800  D   1076 STOX:  LXI    B,S
034B 110000  D   1077        LXI    D,X
034E 2E04        1078        MVI    L,4
0350 0A          1079 STOX1: LDAX   B
0351 12          1080        STAX   D
0352 03          1081        INX    B
0353 13          1082        INX    D
0354 2D          1083        DCR    L
0355 C25003  C   1084        JNZ    STOX1
0358 C9          1085        RET
                 1086 ;
                 1087 ;************************************************************
                 1088 ;
                 1089 ;     TEST FOR MANTISSA = 0
                 1090 ;
                 1091 ;     RETURN ZERO IF MANTISSA = 0
                 1092 ;
                 1093 ;     REGISTER PAIR HL HOLDS MANTISSA ADDRESS
```

```
LOC  OBJ        LINE      SOURCE STATEMENT

1094 ;
                1095 ;
0359 AF         1096 TEST0:  XRA    A
035A B6         1097         ORA    M
035B 23         1098         INX    H
035C B6         1099         ORA    M
035D 23         1100         INX    H
035E B6         1101         ORA    M
035F 23         1102         INX    H
0360 B6         1103         ORA    M
0361 C9         1104         RET
                1105 ;
                1106 ;****************************************************************
                1107 ;
                1108         END
```

PUBLIC SYMBOLS
| | | | | | | | | | | | | | |
|---|---|---|---|---|---|---|---|---|---|---|---|---|---|
| BCDADD | C 0000 | BCDDIV | C 0166 | BCDMUL | C 00DF | BCDSUB | C 00D9 | CHGSNX | C 026E | CLEARX | C 0260 | DIV0 | D 001C |
| EXPX | D 0004 | FIX | C 0239 | LOAD | C 0207 | SIGNX | D 0005 | STORE | C 022A | X | D 0000 | | |

EXTERNAL SYMBOLS

USER SYMBOLS
| | | | | | | | | | | | | | |
|---|---|---|---|---|---|---|---|---|---|---|---|---|---|
| ADD1 | C 0015 | ADD10 | C 00B9 | ADD11 | C 00CF | ADD12 | C 00D5 | ADD2 | C 001E | ADD3 | C 0039 | ADD4 | C 0046 |
| ADD5 | C 006E | ADD6 | C 007B | ADD7 | C 008A | ADD8 | C 00A0 | ADD9 | C 00A9 | BCDADD | C 0000 | BCDDIV | C 0166 |
| BCDMUL | C 00DF | BCDSUB | C 00D9 | CHGSNX | C 026E | CLEARS | C 0276 | CLEARX | C 0260 | CLRS1 | C 027D | CLRX1 | C 0267 |
| CMPR | C 0284 | CMPR1 | C 028C | DIV0 | D 001C | DIV1 | C 0180 | DIV10 | C 0203 | DIV2 | C 0191 | DIV3 | C 01A1 |
| DIV4 | C 01A3 | DIV5 | C 01BE | DIV6 | C 01C7 | DIV7 | C 01D0 | DIV8 | C 01E7 | DIV9 | C 01FA | INY | C 0296 |
| INY1 | C 029E | DNZT | C 02A7 | INZT1 | C 02AF | EXPT | D 0016 | EXPX | D 0004 | EXPY | D 000A | EXPZ | D 0010 |
| FIX | C 0239 | FIX1 | C 0251 | LOAD | C 0207 | LOAD1 | C 0210 | LOAD2 | C 0221 | MUL1 | C 00F4 | MUL2 | C 010D |
| MUL3 | C 010F | MUL4 | C 0123 | MUL5 | C 0135 | MUL6 | C 0146 | MUL7 | C 0159 | MUL8 | C 0162 | NORMX | C 02B8 |
| NORMX1 | C 02BF | NORMY | C 02D3 | NORMY1 | C 02DA | RND6 | C 02EE | RND61 | C 0302 | S | D 0018 | SHIFTL | C 0315 |
| SHIFTR | C 032D | SIGNT | D 0017 | SIGNX | D 0005 | SIGNY | D 000D | SIGNZ | D 0011 | SL1 | C 0319 | SR1 | C 0334 |
| ST1 | C 0230 | STORE | C 022A | STOX | C 0348 | STOX1 | C 0350 | T | D 0012 | TEST0 | C 0359 | X | D 0000 |
| Y | D 0006 | Z | D 000C | | | | | | | | | | |

ASSEMBLY COMPLETE, NO ERRORS
LOC OBJ        LINE     , SOURCE STATEMENT

© 1983 DICKEY-john Corporation--.

```
                1  $ TITLE('MOTOMCO 919 AUTOMATIC ASSEMBLY LANGUAGE SUBROUTINES 26 MAY 83')
                2  $ MOD85
                3  $ DEBUG
                4 ;
                5 ;
                6         NAME    ASMSUB
                7 ;
                8         PUBLIC  CLEAR
                9         PUBLIC  OC
                10 ;
                11        CSEG
                12 ;
0000 C1         13 CLEAR:  POP    B
0001 210080     14         LXI    H,8000H
0004 3E00      15         MVI    A,0
0006 77         16 CLR:   MOV    M,A
0007 2C         17         INR    L
0008 C20600  C  18         JNZ    CLR
```

```
LOC  OBJ        LINE      SOURCE STATEMENT

000B C5          19       PUSH    B
000C C9          20       RET
                 21 ;
                 22 ;
000D F3          23 OC:   DI
000E DB02        24       IN      2
0010 E610        25       ANI     10H
0012 C20D00  C   26       JNZ     OC
0015 CD3300  C   27       CALL    SPACE
0018 0608        28       MVI     B,8
001A 79          29       MOV     A,C
001B 00          30       NOP
001C 00          31       NOP
001D 00          32       NOP
001E 0F          33 OC1:  RRC
001F DC3C00  C   34       CC      MARK
0022 D43300  C   35       CNC     SPACE
0025 05          36       DCR     B
0026 C21E00  C   37       JNZ     OC1
0029 00          38       NOP
002A 00          39       NOP
002B CD3C00  C   40       CALL    MARK
002E CD3C00  C   41       CALL    MARK
0031 FB          42       EI
0032 C9          43       RET
                 44 ;
0033 F5          45 SPACE: PUSH   PSW
0034 3E40        46       MVI     A,40H
0036 30          47       SIM
0037 CD4500  C   48       CALL    DELAY
003A F1          49       POP     PSW
003B C9          50       RET
                 51 ;
003C F5          52 MARK: PUSH    PSW
003D 3EC0        53       MVI     A,0C0H
003F 30          54       SIM
0040 CD4500  C   55       CALL    DELAY
0043 F1          56       POP     PSW
0044 C9          57       RET
                 58 ;
0045 AF          59 DELAY: XRA    A
0046 2A5300  C   60       LHLD    TIME
0049 2B          61 DLY:  DCX     H
004A BD          62       CMP     L
004B C24900  C   63       JNZ     DLY
004E BC          64       CMP     H
004F C24900  C   65       JNZ     DLY
0052 C9          66       RET
                 67 ;
0053 4601        68 TIME: DW      0146H
                 69 ;
                 70       END

PUBLIC SYMBOLS
CLEAR  C 0000    OC    C 000D

EXTERNAL SYMBOLS

USER SYMBOLS
CLEAR  C 0000    CLR   C 0006    DELAY  C 0045    DLY   C 0049   MARK  C 003C   OC   C 000D   OC1   C 001E
SPACE  C 0033    TIME  C 0053

ASSEMBLY COMPLETE,  NO ERRORS
```

The invention is claimed as follows:

1. Apparatus for determining the difference in capacitance between any two given settings on a variable capacitor reference element including a fixed member and a movable member which is continuously rotatable relative to the fixed member to define therebetween a continuously variable capacitance, said apparatus comprising:

stepping means coupled with said movable member for incrementally rotating said movable member a predetermined number of steps of equal angular extent per revolution; control means for incrementally energizing said stepping means in a predetermined fashion so as to achieve said incremental rotation thereof; orienting means for defining a predetermined and repeatable base position of said movable member with respect to said fixed member; and counting means for counting the number of said steps of said stepping means during rotation of said movable member between said base position and any other position of said movable member with respect to said fixed member; whereby said difference in capacitance between any two given settings of said variable capacitor is determined as a function of the number of steps counted by said counting means during said rotation between said base position and each of said given settings, respectively.

2. A measurement apparatus for use with a tester of the type wherein a property of a sample is determined as a function of the change in capacitance of a sample-receiving test cell when a sample is present therein from the capacitance of said test cell when empty, and including a reference oscillator and a test cell oscillator in circuit with said test cell, and a variable capacitor coupled with the test cell and with the oscillators for bringing respective outputs of said two oscillators into a balanced condition both with the test cell empty and with a sample present in the test cell; said variable capacitor comprising a fixed member and a movable member which is rotatable through 360 degrees relative to said fixed member; said measurement apparatus comprising: stepping means coupled with said rotatable member for incrementally rotating said member a predetermined number of steps of equal angular extent per revolution; control means for incrementally energizing said stepping means in a predetermined fashion to achieve said incremental rotation thereof; orienting means for defining a predetermined and repeatable base position of said movable member with respect to said fixed member; and counting means for counting the number of said steps of said stepping means during rotation of said movable member between said base position and any other position of said movable member with respect to said fixed member; whereby the capacitance value between any two given settings of said variable capacitor may be determined as a function of the number of steps counted by said counting means during said rotation between said base position and each of said given settings, respectively.

3. Apparatus according to claim 2 wherein said stepping means includes stepping motor means and gear means intermediate said motor means and said movable member for reducing the angular extent of each increment of movement of said movable member in response to each increment of movement of said stepping motor and thereby achieving said predetermined number of steps of equal angular extent per revolution.

4. Apparatus in accordance with claim 3 wherein said predetermined number of steps of equal angular extent is substantially on the order of 4,800.

5. Apparatus according to claim 2 and further including an AGC loop coupled to each of said oscillators to stabilize the output thereof.

6. Apparatus according to claim 5 wherein each of said oscillators comprises a dual-gate MOSFET, and wherein said reference oscillator further includes a reference crystal element to stabilize the output thereof.

7. Apparatus according to claim 2 and further including sensing means for sensing said balanced condition between said two oscillators; and digital computer means comprising said control means for incrementally energizing said stepping means; said digital computer means also including register means comprising said counting means for counting said steps, and calculating means coupled to said register means and to said sensing means and operative for determining the moisture content of said sample.

8. Apparatus according to claim 7 wherein said digital computer means further includes memory means for containing linearization data corresponding to empirically determined correction factors for substantially linearizing response of the associated variable capacitor, whereby substantially identical moisture measurements are attainable from one apparatus to another.

9. Apparatus according to claim 7 wherein said sensing means comprises test cell circuit means coupled with said test cell, with said variable capacitor, and with said oscillators for detecting said balanced condition and for producing a null signal in response thereto; said balanced condition occuring at a capacitance value defined substantially at mirror image points in the position of said movable member relative to said fixed member of said variable capacitor; said calculating means being operative for determining the position of said movable member substantially one-half way between the smaller arc defined intermediate said mirror image points when the test cell is empty and comprising said base position.

10. Apparatus according to claim 9, said digital computer means further including memory means for recording said base position; said calculating means being further coupled with said memory means for determining the number of steps between said base position and said positions at which said null signal is produced both with a sample absent from said test cell and with a sample present in said test cell to thereby determine the capacitance and moisture content of said sample.

11. Apparatus according to claim 7 and further including amplitude-control means for maintaining the reference oscillator output at a predetermined higher amplitude than the test cell oscillator output, thereby maintaining a positive sense to a differential voltage developed between the two oscillators, said differential voltage comprising said null signal when it reaches a minimum value.

12. Apparatus according to claim 11 wherein said digital computer means further comprises a ground-referenced analog-to-digital converter for receiving said differential voltage.

13. Apparatus according to claim 7 wherein said stepping means comprises a stepping motor responsive to a predetermined input signal for normally achieving a predetermined number of incremental steps per revolution thereof and wherein said digital computer means includes controlled sequence pulse output means for incrementally energizing said stepping motor so as to achieve increments of movements thereof of substantially one-half the angular extent of increments of movement normally achievable in response to said predetermined input signal.

14. Apparatus according to claim 13 wherein said predetermined number of steps normally achieved by said motor is substantially 48, whereby said incremental pulse control means achieves substantially 96 steps per revolution of said motor; and wherein said stepping means further includes reducing gear means having a ratio of substantially 50 to 1 interposed between said stepping motor and said movable member, to thereby define substantially 4800 steps of equal angular extent per revolution of said movable member.

15. Apparatus according to claim 7 wherein said digital computer means further includes electronic memory means for storing a predetermind set of instructions for operation of said apparatus and data for use by said calculating means in determining the moisture content of said sample from the determined position of said variable capacitor; and further including calibrating means for providing additional data for calculating said moisture content for samples of each of a plurality of materials having different moisture-to-capacitance characteristics.

16. Apparatus according to claim 15 wherein said calibrating means comprises plug-in module means including additional memory means for containing said data corresponding to characteristics of different materials and input means in said apparatus for accepting said plug-in module means and the data therefrom.

17. A method for determining the difference in capacitance between any two given settings on a variable capacitor which comprises a fixed member and a movable member which is continuously rotatable relative to said fixed member to define therebetween a continuously variable capacitance, said method comprising: incrementally rotating said movable member a predetermined number of steps of equal angular extent per revolution; defining a predetermined and repeatable base position of said movable member with respect to said fixed member; counting the number of steps of said movable member during rotation thereof between said base position and any other position relative to said fixed member; and determining the difference in capacitance between said any two given settings as a function of the number of steps counted during rotation between said base position and each of said given settings, respectively.

18. Apparatus for feeding a substantially flat electrical cable between two relatively pivotally movable members while maintaining said cable in a substantially unstressed condition throughout relative pivotal movement of said members over a predetermined arc of less than 360 degrees, said apparatus comprising: pivot means comprising a substantially cylindrical, tubular member and complementary bearing means for rotatably receiving said cylindrical tubular member; an axial slot in said cylindrical tubular member for receiving said substantially flat cable therethrough; and a spiral formed in said cable and comprising at least one and one-half turns thereof externally of said slot and circumferentially surrounding said cylindrical tubular member.

19. In a material property tester, apparatus for automatically delivering a pre-measured quantity of sample material to be tested, said apparatus comprising: an open-ended tubular member for receiving said pre-measured quantity of sample material; door means hingedly mounted within said tubular member and having a closed position for retaining said quantity of material and selectively releasable to an open position for releasing by gravity said material to be tested; actuator means movable for alternatively retaining said door means in said closed position and releasing said door means to said open position; solenoid means for operating said actuator means; a housing rigidly coupled to said tubular member and mounting said actuator means and said solenoid means; mounting means for rotatably mounting said housing for sufficient rotational movement to effect closing of said door means by gravity; and sensor means for detecting said rotation of said housing and for responsively activating said solenoid so as to permit movement of said door means to said closed position and thereafter to retain said door means in said closed position.

20. Apparatus according to claim 19 and further including a substantially flat electrical cable for delivering energizing current to said solenoid means and means for maintaining said cable in a substantially unstressed condition without regard to the rotatable movement of said housing and comprising: a substantially cylindrical, tubular member and complementary bearing means for rotatably receiving said cylindrical member, and together comprising said mounting means; a substantially axial slot in said cylindircal, tubular member for receiving said substantially flat cable therethrough; and a spiral formed in said cable and comprising at least one and one-half turns thereof externally of said slot and circumferentially surrounding said cylindrical tubular member.

21. A method of determining a property of a sample of material comprising the steps of: indicating the identity of the material to a test apparatus; measuring a predetermined quantity by weight of the material to comprise a sample; placing the sample into a first receptacle; measuring the temperature of said sample in said first receptacle while simultaneously calibrating said test apparatus in accordance with the indicated identity of the material; automatically delivering the sample from said first receptacle into a second receptacle in response to completion of said temperature measurement and said calibration; and measuring the moisture content of said sample of material in said second receptacle.

22. A method according to claim 21 wherein the step of indicating the identity of the material includes coupling a data-carrying member with said test apparatus and transferring data from said data-carrying member to said test apparatus to identify calibration data corresponding to the identity of the material.

23. A method according to claim 21 wherein the step of measuring the moisture content of said sample includes the step of measuring the change in capacitance of said second receptacle with the sample introduced thereto over the capacitance thereof when empty; and calculating the moisture content of the sample in accordance with a predetermined, known relationship between capacitance and moisture content.

24. A method according to claim 23 wherein the step of calibrating further comprises, prior to the step of delivering the sample material to the second receptacle, determining a repeatable reference point for the measurement of capacitance; measuring the capacitance of the empty second receptacle; measuring the capacitance of a first standard network of a relatively low, known capacitance and of a second standard network of a relatively high, known capacitance; and comparing said capacitance measurements with the known values thereof to reconfirm the accuracy of operation of said test apparatus.

25. A method according to claim 24 wherein the steps of measuring capacitance further include, determining the capacitance value between two settings on a variable capacitor which comprises a fixed member and a movable member, and comprising the further steps of: incrementally rotating said movable a predetermined number of steps of equal angular extent per revolution; defining a predetermined and repeatable base position of said movable member with respect to said fixed member; counting the number of steps of said movable member during rotation thereof between said base position and any other position relative to said fixed member; and determining said capacitance value between said two settings as a function of the number of steps counted during rotation between said base position and each of said given settings respectively.

26. A method according to claim 25 wherein equal capacitance values exist at mirror image positions in the rotation of the movable member, and wherein the steps of measuring capacitance further include measuring the capacitance of the empty second receptacle, of the first standard network, and of the second standard network at each of said mirror image positions during a single 360 degrees rotation of said movable member.

* * * * *